United States Patent
Lagrange et al.

(10) Patent No.: US 6,451,067 B1
(45) Date of Patent: Sep. 17, 2002

(54) DYEING METHOD USING A HETEROCYCLIC CATIONIC AMINE AND A COMPOUND CHOSEN FROM AN ALDEHYDE, A KETONE, A QUINONE, A DI-IMINOISOINDOLINE DERIVATIVE AND A 3-AMINO-ISOINDOLONE DERIVATIVE

(75) Inventors: Alain Lagrange, Coupvray; Hervé Andrean, Paris, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/622,666

(22) PCT Filed: Dec. 22, 1999

(86) PCT No.: PCT/FR99/03248

§ 371 (c)(1), (2), (4) Date: Oct. 27, 2000

(87) PCT Pub. No.: WO00/38641

PCT Pub. Date: Jul. 6, 2000

(30) Foreign Application Priority Data

Dec. 23, 1998 (FR) .............................................. 98 16377

(51) Int. Cl.$^7$ ................................................. A61K 7/13
(52) U.S. Cl. ....................... 8/405; 8/406; 8/409; 8/410; 8/535; 8/607; 8/608; 8/657; 8/426
(58) Field of Search ........................... 8/405, 406, 409, 8/410, 535, 607, 608, 657, 426

(56) References Cited

U.S. PATENT DOCUMENTS

| | | | |
|---|---|---|---|
| 5,034,014 A | * 7/1991 | Wenke | ........................ 8/408 |
| 5,340,366 A | 8/1994 | Lang et al. | ..................... 8/409 |
| 5,616,150 A | 4/1997 | Moeller et al. | ................ 8/405 |
| 5,743,919 A | 4/1998 | Moeller et al. | ................ 8/409 |
| 6,001,135 A | * 12/1999 | Rondeau et al. | ............... 8/407 |
| 6,077,320 A | * 6/2000 | Andrean et al. | ............... 8/405 |

FOREIGN PATENT DOCUMENTS

| | | | |
|---|---|---|---|
| DE | 43 14 317 | 11/1994 | |
| DE | 44 09 143 | 9/1995 | |
| EP | 0 502 783 | 9/1992 | |
| EP | 0 847 749 | 6/1998 | |
| GB | 2 181 740 | 4/1987 | |
| GB | 2181750 A | * 4/1987 | ............ A61K/7/13 |

OTHER PUBLICATIONS

English language Derwent Anstract of EP 0 847 749.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The present invention relates to the use, for dyeing keratin fibres, of at least one heterocyclic cationic amine and of at least one compound chosen from an aldehyde, a ketone, a quinone and a diiminoisoindoline or 3-aminoisoindolone derivative, in order to obtain, by reaction without an oxidizing agent, a coloration of the said keratin fibres. The invention also relates to dye compositions comprising these compounds and to dyeing agents for using them.

76 Claims, No Drawings

DYEING METHOD USING A HETEROCYCLIC CATIONIC AMINE AND A COMPOUND CHOSEN FROM AN ALDEHYDE, A KETONE, A QUINONE, A DI-IMINOISOINDOLINE DERIVATIVE AND A 3-AMINO-ISOINDOLONE DERIVATIVE

The present invention relates to the use, for dyeing keratin fibres, of at least one heterocyclic cationic amine and of at least one compound chosen from an aldehyde, a ketone, a quinone and a diiminoisoindoline or 3-aminoisoindolone derivative, to dye compositions comprising a combination of these compounds, to dyeing processes using the said compounds and to a multi-compartment device containing these compounds.

It is known practice, for the dyeing of keratin fibres, and in particular of human keratin fibres such as the hair, to use direct dyes or coloured substances which give the fibre a temporary or semi-permanent coloration, of low dyeing power, which is generally removed by washing. The ranges of shades obtained by these direct processes are generally limited. It is also known practice to use oxidation dyes (oxidation basis and couplers), which are compounds which are initially colourless or weakly coloured and which, under the action of an oxidizing agent, generate coloured compounds by a process of oxidative condensation. Compared with direct colorations, oxidative colorations are permanent, powerful and withstand external agents (light, bad weather, washing, perspiration and rubbing). Nevertheless, the use of the oxidizing agent can harm the keratin fibres and makes the processes for carrying out the oxidative dyeing operations relatively complex.

The Applicant has just discovered a novel dyeing process, which does not involve a process of oxidative development of dyes, and which given a wide range of shades.

The compounds used by the Applicant are small molecules which can penetrate into keratin easily. The Applicant has found, suprisingly, that those compounds can then condense to form chromophores or dyes, bulkier molecules which remain trapped inside the keratin.

The Applicant has thus found that the dyes obtained withstand shampooing and perspiration and are stable with respect to light, bad weather and chemical agents. These colorations withstand shampooing particularly well. The Applicant has, in a way, discovered a novel dyeing process which has the advantages of so-called oxidation dyeing without exhibiting its drawbacks, since oxidizing agent is used.

One subject of the present invention is thus the use, for dyeing keratin fibres, of a heterocyclic cationic amine and of a compound chosen from an aldehyde, a ketone, a quinone and a diiminoisoindoline or 3-aminoisoindolone derivative.

Another subject of the invention relates to dye compositions comprising these compounds.

A subject of the present invention is also a process for dyeing keratin fibres, which consists in applying a heterocyclic cationic amine and a compound chosen from an aldehyde, a ketone, a quinone and a diiminoisoindoline or 3-aminoisoindolone derivative to the fibres, either simultaneously, in the form of a mixture prepared at the time of use, or successively.

Another subject of the invention also consists of a dyeing agent for carrying out the process of the invention.

Other subjects of the invention will become apparent in the light of the description and the examples which follow.

The main subject of the present invention is thus the use, for dyeing keratin fibres, in particular human keratin fibres such as human hair, of at least one heterocyclic cationic amine and of at least one compound chosen from an aldehyde, a ketone, a quinone and a diiminoisoindoline or 3-aminoisoindolone derivative, in order to obtain, by reaction without an oxidizing agent, a coloration of the said keratin fibres.

For the purposes of the invention, the exxpression "heterocyclic cationic amine" means a molecule comprising at least one amine function, at least one heterocycle, preferably a nitrogenous heterocycle, and at least one positve group, preferably on the heterocycle.

The heterocyclic cationic amine is chosen from the compounds of formula (I) below and the cosmetically acceptable salts thereof:

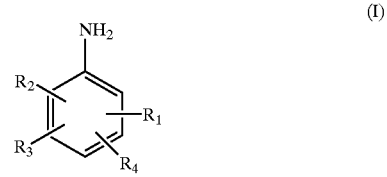

(I)

in which:

$R_1$, $R_2$, $R_3$ and $R_4$, which may be identical or different, represent a hydrogen atom; a halogen atom, an $-NH_2$ group, an -OH group Z; a group Z; a group -COZ; a group -COOZ; an alkylcarbonyl radical; an aminoalkylcarbonyl radical; an N-alkylaminoalkylcarbonyl radical; an N,N-dialkylaminoalkylcarbonyl radical; an aminoalkylcarbonylalkyl radical; an N-alkylaminoalkycarbonylalkyl radical; an N,N-dialkylaminoalkylcarbonylalkyl radical; a carboxyl radical; an alkylcarboxyl radical; an alkylsulphonyl radical; an aminosulphonyl radical; an N-alkylaminosulphonyl radical; an N,N-dialkylaminosulphonyl radical; an aminosulphonylalkyl radical; an N-alkylaminosulphonylalkyl radical; an N,N-dialkylaminosulphonylalkyl radical; a carbamyl radical; an N-alkylcarbamyl radical; an N,N-dialkylcarbamyl radical; a carbamylalkyl radical; an N-alkylcarbamylalkyl radical; an N,N-dialkylcarbamylalkyl radical; an alkyl, monohydroxyalkyl, polyhydroxyalkyl, alkoxyalkyl or trifluoroalkyl radical or a cyano radical; a group $OR_1$, $SR_1$, $OR_1Z$ or $SR_1Z$ or an amino group protected with an alkylcarboxyl, trifluoroalkylcarbonyl, aminoalkylcarbonyl, carbonyl, N-alklaminoalkylcarbonyl, N,N-dialkylaminoalkylcarbonyl, alkylcarboxyl, carbamyl, N-alkylcarbamyl, N,N-dialkylcarbamyl, alkylsulphonyl, aminosulphonyl, N-alkylaminosulphonyl, N,N-dialkylaminosulphonyl, thiocarbamyl or formyl radical, a group -COZ or a group -COOZ;

$R_1$ denotes an alkyl, monohydroxyalkyl or polyhydroxyalkyl radical, a group Z, an alkoxyalkyl radical; an aryl radical; a benzyl radical, a carboxyalkyl radical, an alkoxycarboxyalkyl radical, a cyanoalkyl radical, a carbamylalkyl radical or an N-alkylcarbamylalkyl radical; an N,N-dialkylcarbamylalkyl radical; a trifluoroalkyl radical; an aminosulphonylalkyl radical; an N-alkylaminosulphonylalkyl radical; an N,N-dialkylaminosulphonylalkyl radical; an alkylsulphinylalkyl radical; an alkylsulphonylaklyl radical; an alkylcarbonylalkyl radical; an aminoalkyl radical; an aminoalkyl radical in which the amine is substituted with one or two radicals, which may be identical or different, chosen from alkyl, monohydroxyalkyl, polyhydroxyalkyl, alkylcarbonyl, formyl, trifluoroalkylcarbonyl, alkylcarboxyl, carbamyl, N-alkylcarbamyl, N,N-dialkylcarbamyl, thiocarbamyl and alkylsulphonyl radicals and from the groups Z, -COZ or -COOZ;

Z representing a group of formula (II) or (III) below:

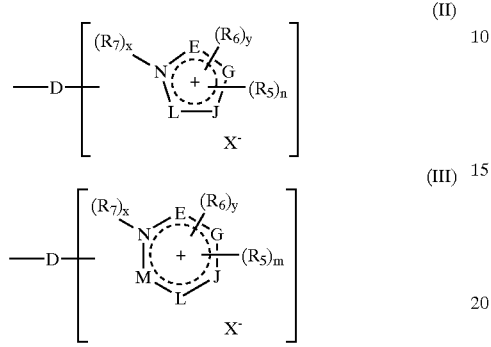

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1-C_6$ alkoxy radicals, and which can bear one or more ketone functions;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals $R_5$, which may be identical or different, represent one of the two valencies of a linker arm D, a second group Z which is identical to or different from the first group Z, a halogen atom, a hydroxyl radical, a $C_1-C_6$ alkyl radical, a $C_1-C_6$ monohydroxyalkyl radical, a $C_2-C_6$ polyhydroxyalkyl radical, a nitro radical, a cyano radical, a cyano($C_1-C_6$)alkyl radical, a $C_1-C_6$ alkoxy radical, a tri($C_1-C_6$)alkylsilane($C_1-C_6$) alkyl radical, an amido radical, an aldehydo radical, a carboxyl radical, a ($C_1-C_6$)alkylcarbonyl radical, a thio radical, a $C_1-C_6$ thioalkyl radical, a $C_1-C_6$ alkylthio radical, an amino radical, an amino radical protected with a ($C_1-C_6$)alkylcarbonyl, carbamyl or $C_1-C_6$ alkyl sulphonyl radical; a group NHR" or NR"RO in which R" and RO, which may be identical or different, represent a $C_1-C_6$ alkyl radical, a $C_1-C_6$ monohydroxyalkyl radical or a $C_2-C_6$ polyhydroxyalkyl radical;

$R_6$ represents one of the two valencies of a linker arm B, a $C_1-C_4$ alkyl radical, a $C_1-C_6$ monohydroxyalkyl radical, a $C_2-C_6$ polyhydroxyalkyl radical, a cyano-($C_1-C_6$)alkyl radical, a tri($C_1-C_6$)alkylsilane($C_1-C_6$) alkyl radical, a ($C_1-C_6$)alkoxy($C_1-C_6$)alkyl radical, a carbamyl($C_1-C_6$)alkyl radical, a ($C_1-C_6$)alkylcarboxy-($C_1-C_6$)alkyl radical, a benzyl radical or a second group Z which is identical to or different from the first group Z;

$R_7$ represents one of the two valencies of a linker arm D, a $C_1-C_6$ alkyl radical; a $C_1-C_6$ monohydroxyalkyl radical; a $C_2-C_6$ polyhydroxyalkyl radical; an aryl radical; a benzyl radical; a $C_1-C_6$ aminoalkyl radical, a $C_1-C_6$ aminoalkyl radical in which the amine is protected with a ($C_1-C_6$)alkylcarbonyl, carbamyl or $C_1-C_6$ alkylsulphonyl radical; a carboxy($C_1-C_6$)alkyl radical; a cyano($C_1-C_6$)alkyl radical; a carbamyl($C_1-C_6$)alkyl radical; a $C_1-C_6$ trifluoroalkyl radical; a tri($C_1-C_6$) alkylsilane($C_1-C_6$)alkyl radical; a $C_1-C_6$ sulphonamidoalkyl radical; a ($C_1-C_6$)alkylcarboxy($C_1-C_6$)alkyl radical; a ($C_1-C_6$)alkylsulphinyl($C_1-C_6$)alkyl radical; a ($C_1-C_6$)alkylsulphonyl($C_1-C_6$)alkyl radical; a ($C_1-C_6$)-alkylketo($C_1-C_6$)alkyl radical; an N-($C_1-C_6$) alkylcarbamyl($C_1-C_6$)alkyl radical; an N-($C_1-C_6$) alkylsulphonamido($C_1-C_6$)alkyl radical;

x and y are integers equal to 0 or 1; with the following conditions;

(i) in the unsaturated cationic groups of formula (II);
when x=0, the linker arm D is attached to the nitrogen atom,
when x=1, the linker arm D is attached to one of the ring members E, G, J or L,
y can take the value 1 only;
1) when the ring members E, G, J and L simultaneously represent a carbon atom and when the radical $R_6$ is borne by the nitrogen atom of the unsaturated ring; or alternatively
2) when at least one of the ring members E, G, J and L represents a nitrogen atom to which the radical $R_6$ is attached;

(ii) in the unsaturated cationic groups of formula (TII):
when x=0, the linker arm D is attached to the nitrogen atom,
when x=1, the linker arm D is attached to one of the ring members E, G, J, L or M,
y can take the value 1 only when at least one of the ring members E, G, J, L and M represents a divalent atom and when the radical $R_6$ is borne by the nitrogen atom of the unsaturated ring;

$X^-$ represents a monovalent or divalent anion and preferably represents a halogen atom such as chlorine, bromine, fluorine or iodine, a hydroxide, a hydrogenosulphate or an alkyl sulphate such as, for example, a methyl sulphate or an ethyl sulphate; and the compound (I) defined above contains at least one group Z.

In formula (I) above, the alkyl and alkoxy radicals can be linear or branched; the amino radicals can optionally be salified with strong mineral acids such as HCl, HBr or $H_2SO_4$, or organic acids such as acetic acid, lactic acid, citric acid or succinic acid.

Among the rings of the unsaturated groups Z of formula (II) above which may be mentioned in particular, by way of example, are pyrrole, imidazole, pyrazole, oxazole, thiazole and triazole rings.

Among the rings of the unsaturated groups Z of formula (III) above which may be mentioned in particular, by way of example, are pyridine, pyrimidine, pyrazine, oxazine and triazine rings.

Among the compounds of formula (I) which may be mentioned in particular are:

1-[3-((2,4-diaminophenoxy)propyl]-3-methyl-3H-imidazole-1-ium chloride;

1-[(3-hydroxy-4-methylphenylcarbamoyl)methyl]-3-methyl-3H-imidazol-1-ium chloride;

3-ethyl-1-[(3-hydroxyphenylcarbamoyl)methyl]-3H-imidazol-1-ium chloride;

1-[(3-hydroxy-2,4-dimethylphenylcarbamoyl)methyl]-3-methyl-3H-imidazol-1-ium chloride;

1-[(4-chloro-3-hydroxyphenylcarbamoyl)methyl]-3-ethyl-3H-imidazol-1-ium chloride;
1-[(3-hydroxy-4-methoxyphenylcarbamoyl)methyl]-3-methyl-3H-imidazol-1-ium chloride;
1-[(3-hydroxy-4-methylphenylcarbamoyl)methyl]-2-methyl-2H-pyrazol-1-ium chloride;
1-[2-(3-hydroxy-4-methylphenylamino)ethyl]-3-methyl-3H-imidazol-1-ium bromide;
1-[2-(3-hydroxy-4-methylphenylcarbamoyloxy)ethyl]-2,3-dimethyl-3H-imidazol-1-ium chloride;
1-{[3-amino-4-(3-(3-methyl-3H-imidazol-1-ium)-propoxy)phenylcarbamoyl]methyl}-3-methyl-3H-imidazol-1-ium dichloride;
3-(3-trimethylammonium-2-hydroxypropyl)-1-[(3-hydroxy-4-methylphenylcarbamoyl)methyl]-3H-imidazol-1-ium dichloride;
1-{[2-(2,4-diaminophenoxy)ethylcarbamoyl]methyl}-3-methyl-3H-imidazol-1-ium chloride;
1-[(2,4-dihydroxyphenylcarbamoyl)methyl]-3-methyl-3H-imidazol-1-ium chloride;
N,N-bis[2-(3-methyl-3H-imidazol-1-ium)ethyl]benzene-1,3-diamine dichloride;
1-{3-[4-amino-2-(2-triethylammoniumacetylamino)-phenoxy]propyl}-3-methyl-3H-imidazol-1-ium dichloride;
1-(3-{4-amino-2-[2-(3-methyl-3H-imidazol-1-ium)-acetylamino]phenoxy}propyl)-1,4-dimethylpiperazin-1-ium dichloride;
1-[2-(2,4-dihydroxyphenyl)-2-oxoethyl]-3-methyl-3H-imidazol-1-ium chloride;
1-[2-(2,4-diaminophenyl)ethyl]-3-methyl-3H-imidazol-1-ium chloride;
1,4-bis-1-{3-[3-(2,4-diaminophenoxy)propyl]-3H-imidazol-1-ium}butane dichloride monohydrate;
1,3-bis[3-(2,4-diaminophenoxy)propyl]-3H-imidazol-1-ium chloride;
3-[3-(2,4-diaminophenoxy)propyl]-1[(3-hydroxy-4-methylphenylcarbamoyl)methyl]-3H-imidazol-1-ium chloride;
1,4-bis{3-[(3-hydroxy-4-methylphenylcarbamoyl)-methyl]-3H-imidazol-1ium}butane dichloride;
1,4-bis-{3-[2-(2,4-diaminophenyl)ethyl]-3H-imidazol-1-ium}butane dichloride;
1,4-bis-{3-[2-(3-hydroxy-4-methylphenylamino)ethyl]-3H-imidazol-1ium}butane dibromide;
1,4-bis{3-[(2,4-dihydroxyphenylcarbamoyl)methyl]-3H-imidazol-1-ium}butane dichloride;
3-[3-(2,4-diaminophenoxy)propyl]-1-[(2,4-dihydroxyphenylcarbamoyl)methyl]-3H-imidazol-1-ium chloride;
3-[3-(2-aminophenylamino)propyl]-1-methyl-3H-imidazol-1-ium monochloride;
3-[2-(2-amionphenylamino)ethyl]-1-methyl-3H-imidazol-1-ium monochloride;
4-[2-(1-methyl-3H-imidazol-1-ium)ethoxy-N2-[2-(1-methyl-3H-imidazol-1-ium)ethyl]benzene-1,2-diamine dichloride;
3-[2-(2-amino-4-methyl-phenylamino)ethyl]-1-ethyl-3H-imidazol-1-ium monochloride;
3-[3-(2-aminophenylamino)propyl]-1-(3-trimethylammonium-2-hydroxypropyl)-3H-imidazol-1-ium dichloride;
3-[3-(2-aminophenylamino)propyl]-1-(2-hydroxyethyl)-3H-imidazol-1-ium monobromide;
3-{[2-(2-aminophenylamino)ethylcarbamoyl]methyl}-1-methyl-3H-imidazol-1-ium monochloride;
1-[2-(2-amino-4-chlorophenylamino)ethyl]pyridinium monochloride;
3-[2-(2-amino-5-methoxyphenylamino)ethyl]-1-methyl-3H-imidazol-1-ium monochloride;
3-[2-(2-amino-5-methylsulphanylphenylamino)ethyl]-1-methyl-3H-imidazol-1-ium monochloride;
1-[2-(4-aminophenylamino)ethyl]-3-methyl-3H-imidazol-1-ium bromide;
1-[3-(2,5-diaminophenoxy)propyl]-3-methyl-3H-imidazol-1-ium chloride;
3-[3-(4-aminophenylamino)propyl]-1-methyl-3H-imidazol-1-ium chloride;
3-[3-(4-amino-3-methylphenylamino)propyl]-1-methyl-3H-imidazol-1-ium chloride;
3-[3-(4-amino-2-methylphenylamino)propyl]-1-methyl-3H-imidazol-1-ium chloride;
3-[3-(4-amino-2-fluorophenylamino)propyl]-1-methyl-3H-imidazol-1-ium chloride monohydrate;
3-[3-(4-amino-3-cyanophenylamino)propyl]-1-methyl-3H-imidazol-1-ium chloride;
1-[2-(4-amino-2-methoxyphenylamino)ethyl]-3-methyl-3H-imidazol-1-ium chloride;

and the addition salts thereof with an acid.

The compounds use as compounds of formula (I) are preferaby chosen from:

1-(5-amino-2-hydroxybenzyl)-3-methyl-3H-imidazol-1-ium chloride;
1-(5-amino-2-hydroxybenzyl)-2-methyl-2H-pyrazol-1-ium chloride;
1-[2-(2,5-diaminophenyl)ethyl]-3-methyl-3H-imidazol-1-ium chloride;
1,3-bis-1-{3-{3'-[(4"-amino-3"-methylanilino)-N-propyl]}-3H-imidazol-1-ium}propane dichloride;
1,3-bis-1-{3-{3'-[(4"-amino-2"-methylanilino)-N-propyl]}-3H-imidazol-1-ium}propane dichloride monohydrate diethanol;
1,3-bis-1-{3-{3'[(4"-aminoanilino)-N-propyl]}-3H-imidazol-1-ium}propane dichloride monohydrate ethanol;
1,3-bis-1-{3-{3'-[(4"-amino-2"-methylanilino)-N-propyl]}-3H-imidazol-1-ium}-2-propanol dichloride monohydrate;
1,4-bis-1-{3-[3-(2,5-diaminophenoxy)propyl]-3H-imidazol-1-ium}butane dichloride dihydrate;
1,3-bis[3-(3,5-diaminophenoxy)propyl]-3H-imidazol-1-ium monochloride monohydrate;
1,4-bis-1-[3-(5-amino-3-hydroxybenzyl)-3H-imidazol-ium]butane dichloride monohydrate;
1,3-bis{3-{3-[(2-aminoanilino)-N-propyl]}-3H-imidazol-1-ium}propane dibromide;
1,4-bis{3-{2-[(2-aminoanilino)-N-ethyl]}-3H-3H-imidazol-1-ium}butane dichloride;
1-[2-(2-aminoanilino)ethyl]-3-[3-(3-aminoanilino)-propyl]-3H-imidazol-1-ium monochloride;

and the addition salts therof with an acid.

The aldehyde can correspond to formula (IV) below:

(IV)

in which:

$R_8$ denotes a group of formula (IV A) below:

$$\left[\begin{array}{c}R_9\\\phantom{X}\\R_{11}\diagup\!\!\diagdown R_{10}\end{array}\right]_n$$
(IV A)

in which:

$R_9$ and $R_{10}$, which may be identical or different, denote a hydrogen atom or an alkyl, mono- or polyhydroxyalkyl, alkylhydroxyalkyl, alkoxy, $CP_2$ or $OCP_2$ group, $R_9$ and $R_{10}$ can also form, together with the atoms to which they are attached, an aryl ring or a 5 or 6 membered heterocyclic ring, it being possible for the said rings to be substituted or unsubstituted; n denotes an integer from 0 to 3, $R_{11}$ denotes the substituents denoted by $R_9$, a substituted or unsubstituted aryl or alkylaryl group or a substitued or unsubstituted 5- or 6-membered heterocyclic group, or to the cosmetically acceptable salts of these compounds.

The ketone can be chosen from the ketones of formula (V) or (VI) below:

$$\underset{R_{12}\quad R_{13}}{\overset{O}{\underset{\|}{C}}}$$
(V)

$$\underset{R_{12}\quad R_{13}}{\overset{O\quad O}{\underset{\|\quad\|}{C-C}}}$$
(VI)

in which:

$R_{12}$ denotes the substituents denoted by $R_9$, $R_{13}$ denotes an alkyl, mono- or polyhydroxyalkyl or alkylhydroxyalkyl group, or a substituted or unsubstituted aryl, alkylaryl or 5- or 6-membered heterocyclic group, $R_{12}$ and $R_{13}$ also form, together with the atoms to which they are attached, a 5- or 6-membered aryl ring or a heterocyclic ring comprising hetero atoms such as N or S, it being possible for the said ring itself to be attached to a 5- or 6-membered aryl ring or to a heterocycle comprising hetero atoms such as N or S, it being possible for the said rings to be substituted or unsubstituted, or to the cosmetically acceptable salts of these compounds.

The quinone can correspond to formulae (VII) and (VIII) below:

(VII)

(VIII)

in which:

$R_{14}$ denotes a hydrogen or halogen atom or a sulphonic or alkoxy group, $R_{15}$, $R_{16}$ and $R_{17}$, which may be identical or different, denote a hydrogen or halogen atom, a hydroxyl, alkyl, mono- or polyhydroxyalkyl, alkylhydroxyalkyl, alkylsulphonyl, carboxyalkyl, aminoalkyl, alkylaminoalkyl, (dihydroxy)alkylaminoalkyl or alkyl-NR'R" group (with R' and R" denoting alkyl or possibly forming, together with the nitrogen atom to which they are attached, an aryl ring or a 5- or 6-membered heterocycle), an aryl group or an amino group which can be substituted with an alkyl or a hydroxyalkyl, $R_{14}$ and $R_{15}$, $R_{15}$ and $R_{16}$ or $R_{16}$ and $R_{17}$ can form, together with teh atoms to which they are attached, a substituted or unsubstituted aryl ring or 5- or 6-membered heterocycle; or to the cosmetically acceptable salts of these compounds.

The diiminosoindoline or 3-aminosoindolone derivatives can be those corresponding to formula (IX) below:

(IX)

in which:

$R_{18}$ and $RR_{19}$, which may be identical or different, denote a hydrogen atom, an alkyl, mono- or polyhydroxyalkyl, alkylhydroxyalkyl, aminoalkyl, alkylaminoalkyl or (dihydroxy)alkylaminoalkyl group or an alkyl-NR'R" group, with R' and R" denoting alkyl or possibly forming, together with the nitrogen atom to which they are attached, an aryl ring or a 5- or 6-membered heterocycle), A denotes an oxygen atom or NH, X and Z together form a substitued or unsubstituted aryl ring or 5- or 6-membered heterocycle; or to the cosmetically acceptable salts of these compounds.

Among the preferred compounds of formula (IV) which may be mentioned in particular are benzaldehyde, 2,3,4-monohydroxybenzaldehydes, 2,3,4-monomethoxybenzaldehydes, 2,3,4-monomethylbenzaldehydes, (2,3)-, (2,4)-, (2,5)-, (2,6)-, and (3,5)-dihydroxy-benzaldehydes, (2,3)-, (2,4)-, (2,5)-, (2,6)- and (3,5)-dimethoxybenzaldehydes, vanillin, isovanillin, syringaldehyde, ortho-, iso and terephthalaldehyde, (2,3)-, (2,4)-, (2,5)-, (2,6)- and (3,5)-dimethylbenzaldehydes, 4-isopropylbenzaldehyde, 4-dimethylaminobenzaldehyde, 4-diethylaminobenzaldehyde, piperonal, (2,6)- and (3,5)-dimethyl-4-hydroxy-benzaldehyde, 2,3,4-mononitrobenzaldehydes, 2-hydroxy-3-methoxybenzaldehyde, 2-hydroxy-4-methoxybenzaldehyde, 2-hydroxy-5-methoxybenzaldehyde, 2-hydroxy-6-methoxybenzaldehyde, 4-methylthiobenzaldehyde, (2,3,4)-, (2,4,6)-, (3,4,5)- and (2,4,5)-trihyroxybenzaldehydes, methyl 2-, 3- and 4-formyl benzoates, 2,3,4-mono(2-hydroxyethoxy)benzaldehydes, 4-nitro-3-hydroxybenzaldehyde, 3-nitro-4-hydroxybenzaldehyde, 2-nitro-4-hydroxybenzaldehyde, 3-nitro-2-hydroxybenzaldehyde, 2,3,4-monotrifluorobenzaldehydes, 2,3-dihydroxy-4-methoxybenzaldehyde, 3,4-dihydroxy-5-methoxybenzaldehyde, 3,5-dihydroxy-4-methoxybenzaldehyde, 3-methoxy-2-nitrogenzaldehyde, 4-methoxy-3-nitrobenzaldehyde, (2,3,4)-, (2,4,6)-, (3,4,5)- and (2,4,5)-trimethoxybenzaldehydes, 5-nitrovanillin, (2,4)- and (2,6)-dinitrobenzaldehydes, pentamethylbenzaldehyde, 4-methylsulphonylbenzaldehyde, 2,3,4-monoformylphenoxy-acetic acids, 4-diethylaminosalicylaldehyde, 4-(3-dimethylaminopropoxy)benzaldehyde, 2,3-dihydrobenzo-(b)furan-5-carboxaldehyde, 1- and 2-naphthaldehyde, 6- and 5-carboxaldehyde-1,4-benzodioxane, 2,4-monohydroxy-1-naphthaldehydes, 1-monohydroxy-2-naphthaldehyde, 2-(4-formylphenyl)imidazole, 4-pyrrolidinobenzaldehyde, 2,4-monomethoxy-1-naphthaldehydes, 2,3-dimethylchroman-6-carboxaldehyde, 2,3,6,7-tetrahydro-1H,5H-pyrido-(3,2,1-IJ)quinoline-γ-carbaldehyde, 4-dimethylamino-1-naphthaldehyde, 9-anthraldehyde, 3-nitro-4-pyrrolidino benzaldehyde, 3-nitro-4-piperidinobenzaldehyde, 3-nitro-4-morpholinobenzaldehyde, pyridine-2,3,4-monocarboxaldehyde, 2,6-pyridinodicarboxaldehyde, 5-formyl-6-methyluracil, pyridoxal, quinoline-2,3,4-monocarboxaldehydes, 8-hydroxyquinoline-2-carboxaldehyde, 2- and 3-furaldehydes, 2- and 3-thionylcarboxaldehydes, 2- and 3-imidazocarboxaldehydes, 2-pyrrolecarboxaldehyde, 5-nitro-2-furaldehyde, 5-(dimethylamino)-2-furaldehyde, 2,5- and 2,3-thiophenedicarboxaldehydes, pyrazole-3-carbaldehyde, 5-nitro-2-thiophenecarboxaldehyde, 5-nitro-3-thiophenecarboxaldehyde, indole-3-carboxaldehyde, N-methylindole-3-carboxaldehyde, 2-methylindole-3-carboxaldehyde, 4,5,6,7-monomethylindolecarboxaldehyde and 5-formyl-2-furansulphonic acid.

The ketones of formulae (V) and (VI) can be chosen from 2,3-indolinedione, 2,3-butanedione, 2,3-pentanedione, (2,3)- and (3,4)-hexanedione, 1-phenyl-1,2-propanedione, benzil, furil, 2,2'-pyridil, nitrobenzil, anisil, 3,3'-dimethoxybenzil, 4,4'-bis-(dimethylamino)benzil, camphoroquinone, cyclohexane-1,2-dione, isatin, N-methylisatin, 4,5,6,7-monomethylisatin, (4,5)-, (4,7)-, (5,7)- and (6,7)-dimethylisatin, N-ethylisatin, N-hydroxymethylisatin, 5-, 6- and 7-monomethoxyisatin, 4-, 5-, 6- and 7-monochloroisatin, 4-, 5-, 6- and 7-monobromoisatin, N-isopropylisatin, N-butylisatin, N-propylisatin, 5-nitroisatin, isatin-5-sulphonic acid, 2,4,5-trihydroxypyrimidine, alloxan, 1,3-dimethylhexahydro-2,4,5,6-pyrimidinetetraone, ninhydrin, chinisatin, 1,3-indenedione, squaric acid, croconic acid, 3,4-dimethoxy-3-cyclobutene-1,2-dione, 3- and 4-ethoxy-3-cyclobutene-1,2-dione, 3- and 4-isopropoxy-3-cyclobutene-1,2-dione, 3,4-di-N-butoxy-3-cyclobutene-1,2-dione, rhodizonic acid, oxindole, N-methyl-2-indolinone, N-methylnitro-2-indolinone, 6-methoxyoxindole, 5,6-dimethoxyoxindole and 5- and 6-monochlorooxindole.

The preferred quinones of formulae (VII) and (VIII) are, inter alia, 1,4-naphthoquinone, apinulosin, atromentin, aurentiogliocladin, 2,5-dihydroxy-6-methylbenzoquinone, 2-hydroxy-3-methyl-6-methoxybenzoquinone, 2,5-dihydroxy-3,6-diphenylbenzoquinone, 2,3-dimethyl-5-hydroxy-6-methoxybenzoquinone, 2,5-dihydroxy-6-isopropylbenzoquinone, lawsone, juglone, fafioline, naphthazarine, naphthopurpurine, lapachol, plumbagin, chloroplumbagin, droserone, shikonine, 2-hydroxy-3-methyl-1,4-naphthoquinone, 3,5-dihydroxy-1,4-naphthoquinone, 2,5-dihydroxy-1,4-naphthoquinone, 2-methoxy-5-hydroxy-1,4-naphthoquinone, 3-methoxy-5-hydroxy-1,4-naphthoquinone, (1,4)- and (1,2)-napthoquinone, 3-methoxy-5-hydroxy-1,4-naphthoquinone, (1,4)- and (1,2)-naphthoquinone, 4,5-dimethoxy-1,2-benzoquinone, phenanthrenequinone and (1,2)-naphthoquinone-4-sulphonic acid.

The derivatives of formula (IX) are represented in particular by 3-imino-3H-isoindolylamine, 3-imino-4-methyl-3H-isoindol-1-ylamine, 3-imino-4-tert-butyl-3H-isoindol-1-ylamine, 3-imino-7-nitro-3H-isoindol-1-ylamine, 3-amino-1-imino-1H-isoindol-4-ol, 3-imino-7-isopropoxy-3H-isoindol-1-ylamine, 3-imino-7-(2,2,2-trifluoroethoxy)-3H-isoindol-1-ylamine, 3-imino-7-ethoxy-3H-isoindol-1-ylamine, 3-imino-7-butoxy-3H-isoindol-1-ylamine, 3-amino-1-imino-1H-isoindole-4-sulphonic acid, 3-imino-7-chloro-3H-isoindol-1-ylamine, 3-imino-5-methyl-3H-isoindol-1-ylamine, 3-imino-5-ethyl-3H-isoindol-1-ylamine, 3-imino-5-tert-butyl-3H-isoindol-1-ylamine, 3-imino-5-amino-3H-isoindol-1-ylamine, N-(1-amino-3-imino-3H-isoindol-5-yl)acetamide, 3-imino-5-nitro-3H-isoindol-1-ylamine, 3-imino-5-fluoro-3H-isoindol-1-ylamine, 3-imino-5-chloro-3H-isoindol-1-ylamine, 3-imino-5-methylsulphanyl-3H-isoindol-1-ylamine, 3-imino-5-methoxy-3H-isoindol-1-ylamine, 3-imino-5-ethoxy-3H-isoindol-1-ylamine, 3-imino-5-propoxy-3H-isoindol-1-ylamine, 3-imino-5-isopropoxy-3H-isoindol-1-ylamine, 3-imino-5-butoxy-3H-isoindol-1-ylamine, 3-imino-5-isobutoxy-3H-isoindol-1-ylamine, 3-imino-5-tert-butoxy-3H-isoindol-1-ylamine, 3-imino-5-(2,2,2-trifluoromethyl)-3H-isoindol-1-ylamine, 3-imino-5-(2,2,2-trifluoroethoxy)-3H-isoindol-1-ylamine, 3-imino-5-methanesulphonyl-3H-isoindol-1-ylamine, 3-imino-5,6-dimethyl-3H-isoindol-1-ylamine, 3-imino-5,6-diethyl-3H-isoindol-1-ylamine, 3-imino-5,6-dimethoxy-3H-isoindol-1-ylamine, 3-imino-5,6-diethoxy-3H-isoindol-1-ylamine, 3-imino-5,6-dibutoxy-3H-isoindol-1-ylamine, 3-imino-5,6-bis(trifluoromethyl)-3H-isoindol-1-ylamine, 3-imino-5,6-dichloro-3H-isoindol-1-ylamine, 5,6-bis(ethoxymethyl)3-imino-3H-isoindol-1-ylamine, 3-amino-1-imino-1H-isoindole-4,7-diol, 4,7-dichloro-3-imino-3H-isoindol-1-ylamine, 4,5,7-trichloro-3-imino-N6,N6-dimethyl-3H-isoindole-1,6-diamine, 4,5,6,7-tetrachloro-3-imino-3H-isoindol-1-ylamine, 4,5,6,7-tetrafluoro-3-imino-3H-isoindol-1-ylamine, 3-butylimino-3H-isoindol-1-ylamine, 2-(3-aminoisoindol-1-ylideneamino)-ethanol, 3-(3-aminoisoindol-1-ylideneamino)-3-methylpentane-1,5-diol, N-(3-aminoisoindol-1-ylidene)-guanidine, 7-imino-7H-pyrrolo[3,4-b]pyrid-5-ylamine, 7-imino-7H-pyrrolo[3,4-b]pyrazine-5-ylamine, 7-imino-2,3-dimethyl-7H-pyrrolo[3,4-b]pyrazin-5-ylamine, 7-imino-7H-[1,4]dithiino[2,3-c]pyrrol-5-ylamine, 7-imino-2,3-dimethyl-7H-[1,4]dithiino[2,3-c]pyrrol-5-ylamine, 7-imino-2,3-dihydro-7H-[1,4]dithiino[2,3-c]pyrrol-5-ylamine, 3-aminoisoindol-1-one, 3-amino-7-methylisoindol-1-one, 3-amino-7-hydroxymethylisoindol-1-one, 3-amino-7-chloroisoindol-1-one, 3-amino-4-chloroisoindol-1-one, 3-amino-1-oxo-1H-isoindole-4-sulphonic acid, 3-amino-4-nitroisoindol-1-one, 3-amino-6-nitroisoindol-1-one, 3-amino-6-methylisoindol-1-one, 3-amino-6-methylsulphanylisoindol-1-one, 3-amino-6-methoxyisoindol-1-one, 3-amino-5-chloroisoindol-1-one, 3-amino-5-fluoroisoindol-1-one, 3-amino-5-methoxyisoindol-1-one, 3-amino-5-nitroisoindol-1-one, ethyl 3-amino-1-oxo-1H-isoindole-5-carboxylate, 3-amino- 5,6-dichloroisoindol-1-one, 3-amino-5,6-dibromoisoindol-1-one, 3-amino-4,7-dichloroisoindol-1-one, 3-amino-4,5,7-trichloroisoindol-1-one, 3-amino-4,5,6,7-tetrachloroisoindol-1-one, 3-amino-4,5,7-trichloro-6-methylsulphanylisoindol-1-one, 3-amino-4,5,6,7-tetrabromoisoindol-1-one, 3-amino-4,5,6,7-tetrafluoroisoindol-1-one, 3-methylaminoisoindol-1-one, 3-ethylaminoisoindol-1-one, 3-propylaminoisoindol-1-one, 3-dimethylaminoisoindol-1-one, 7-ethylaminopyrrolo[3,4-b]pyrid-5-one, 7-aminopyrrolo[3,4-b]pyrid-5-one, 3-aminopyrrolo[3,4-c]pyrid-5-one, 3-amino-6-methylpyrrolo[3,4-c]pyrid-1-one, 5-aminopyrrolo[3,4-b]pyrid-7-one, 7-aminopyrrolo[3,4-b]pyrazin-5-one, 7-amino-2-methylpyrrolo[3,4-b]pyrazin-5-one, 7-amino-2,3-dimethylpyrrolo[3,4-b]pyrazin-5-one, 7-amino-2,3-dihydro[1,4]dithiino[2,3-c]pyrrol-5-one, 3-imino-2-methyl-2,3-dihydroisoindol-1-one, 3-imino-2-ethyl-2,3-dihydroisoindol-1-one, 3-imino-2-propyl-2,3-dihydroisoindol-1-one, 2-hydroxymethyl-3-imino-2,3-dihydroisoindol-1-one, 2-(2-hydroxyethyl)-3-imino-2,3-dihydroisoindol-1-one, 2-(1-imino-3-oxo-1,3-dihydroisoindol-2-yl)ethanesulphonic acid, 3-(1-imino-3-oxo-1,3-dihydroisoindol-2-yl)propionic acid, 2-(3-hydroxypropyl)-3-imino-2,3-dihydroisoindol-1-one and 5-imino-6-methyl-5,6-dihydropyrrolo[3,4-b]pyridin-7-one.

In the context of the present invention:

The halogen atoms preferentially denote a fluorine, chlorine, bromine or iodine atom.

The alkyl, monohydroxyalkyl, polyhydroxyalkyl, alkylhydroxyalkyl, alkylsulphonyl, carboxyalkyl, aminoalkyl, alkylaminoalkyl and dihydroxyaminoalkyl radicals can be linear or branched.

The alkyl groups in particular denote groups of 1 to 20 carbon atoms such as, for example, methyl, ethyl, propyl, isopropyl, n-propyl, butyl, n-butyl, tert-butyl, pentyl, n-pentyl, isopentyl, n-hexyl, isohexyl, heptyl, octyl, nonyl, decyl, undecyl, dodecyl and pentadecyl groups. The alkyl groups preferably denote a group of 1 to 6 carbon atoms; these alkyl groups can be substituted; for example, with a halogen atom or a cyano or hydroxyl radical, and can thus represent trifluoromethyl, δ-chloropropyl, β-cyanoethyl or β-hydroxyethyl radicals.

Among the monohydroxyalkyl groups which may be mentioned in particular are hydroxymethyl, hydroxyethyl, hydroxypropyl and hydroxybutyl groups.

Among the polyhydroxyalkyl radicals which may be mentioned in particular are dihydroxyethyl, dihydroxypropyl, trihydroxypropyl and dihydroxybutyl radicals.

The alkoxy groups denote a group —O—R, R representing an alkyl group as defined above.

The alkenyl groups denote a monovalent radical corresponding to the ethylenic carbons, such as, for example, alkyl or 3,3-dimethylallyl.

The acetyloxy groups denote a group —O—CO—R, R representing an alkyl group as defined above.

Among the cycloalkyl radicals which may be mentioned in particular are cyclohexyl and cyclopentyl.

Among the aryl radicals, which may be mono- or polycyclic, mention may be made in particular of phenyl and naphthyl groups.

Among the heterocycles and in particular the 5- or 6-membered rings, which may be mono- or polycyclic and containing one or more hetero atoms, mention may be made of thiophene, pyrrole, imidazole, pyrazole, triazole, thiazole, furan, benzofuran, benzimidazole, benzothiazole, pyridyl, benzoxazole, quinolyl, quinazolyl, quinoxalyl, pyrrolidine, piperidine, piperazine and morpholine rings.

Among the alkylaryl radicals which may be mentioned in particular are benzyl, phenethyl and naphthyl methyl groups.

The aminoaryl groups denote groups $NH_3$—R, R representing an aryl radical.

In the context of the present invention, the cycloalkyl and aryl radicals and the heterocycles may be substituted or polysubstituted, for example with a halogen, with a $C_1$–$C_6$ alkyl or monohydroxyalkyl, a $C_2$–$C_6$ polyhydroxyalkyl radical, a $C_1$–$C_6$ alkoxy, a nitro group, a hydroxyl group, a carboxylic group, a $C_1$–$C_4$ acetyloxy group, a carboxamide group, a sulphonamide, sulphonic, nitrile, —$CF_3$ or —$OCF_3$ group, a cyano radical, a cyano-($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehyde radical, a ($C_1$–$C_8$) alkylcarbonyl radical, a thio radical, a $C_1$–$C_6$ thioalkyl radical, a $C_1$–$C_6$ alkylthio radical, an amino radical or an amino radical protected with a ($C_1$–$C_8$)alkylcarbonyl, carbamyl or $C_1$–$C_6$ alkylsulphonyl radical.

In the context of the present invention, the formulae (I) to (IX) are not limited to those specifically described, but also comprise the tautomeric forms thereof, when they exist.

For the purposes of the present invention, the cosmetically acceptable salts of the abovementioned compounds can be hydrochlorides, sulphates, hydrobromides or tartrates.

The compositions for dyeing keratin fibres, in particular human keratin fibres such as the hair, in accordance with the present invention are essentially characterized in that they comprise at least one heterocyclic cationic amine as defined above and at least one compound chosen from an aldehyde, a ketone, a quinone and a diiminoisoindoline or 3-aminoisoindolone derivative as defined above, in a medium which is suitable for dyeing.

In one preferred embodiment of the invention, the compound chosen from an aldehyde, a ketone, a quinone and a diiminoisoindoline or 3-aminoisoindolone derivative is chosen from 1,4-dimethylaminobenzaldehyde and 4-dimethylaminonaphthaldehyde.

The heterocyclic cationic amine can be present in a concentration ranging from 0.01% to 10% and preferably between 0.05% and 5% by weight relative to the total weight of the composition.

The compound chosen from an aldehyde, a ketone, a quinone and a diiminoisoindoline or 3-aminoisoindolone derivative can be present in a concentration ranging from 0.01% to 10% and preferably from 0.05% to 5% by weight relative to the total weight of the composition.

The medium which is suitable for dyeing is preferably an aqueous medium consisting of water and/or of cosmetically acceptable organic solvents, and more particularly alcohols such as ethyl alcohol, isopropyl alcohol, benzyl alcohol and phenyl ethyl alcohol, or glycols or glycol ethers such as propylene glycol or its ethers such as, for example, propylene glycol monomethyl ether, butylene glycol, dipropylene glycol and diethylene glycol alkyl ethers such as, for example, diethylene glycol monoethyl ether or monobutyl ether, in concentrations of between about 0.5% and 20%, and preferably between about 2% and 10%, by weight relative to the total weight of the composition.

Fatty amides such as mono- and diethenolamides of acids derived from copra, of lauric acid or of oleic acid can also be added to the composition according to the invention, in concentrations of between about 0.05% and 10% by weight.

Surfactants that are well known in the prior art and of anionic, cationic, nonionic, amphoteric or zwitterionic type or mixtures thereof can also be added to the composition according to the invention, preferably in a proportion of between about 0.1% and 50% by weight and advantageously between about 1% and 20% by weight relative to the total weight of the composition.

Thickeners can also be used in a proportion ranging form about 0.2% to 20%.

The said de composition can also contain various common adjuvants such as antioxidants, fragrances, sequestering agents, dispersants, hair conditioners, preserving agents and opacifiers, as well as any other additive usually used in the dyeing of keratin substances.

Needless to say, a person skilled in the art will take care to select the optional additional compound(s) mentioned above, such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 2 to 11 and preferably from 5 to 10, and it being possible for it to be adjusted by means of basifying or acidifying agents or buffers that are well known hitherto.

Basifying agents which may be mentioned are aqueous ammonia, alkaline carbonates, alkanolamines, for example mono-, di- and triethanolamine and derivatives thereof, sodium hydroxide, potassium hydroxide and the compounds of formula:

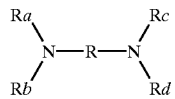

in which R is a propylene residue optionally substituted with a hydroxyl group or a $C_1$–$C_4$ alkyl radical; Ra, Rb, Rc and Rd, simultaneously or independently of each other, represent a hydrogen atom or a $C_1$–$C_4$ alkyl or $C_1$–$C_4$ hyroxyalkyl radical.

The acidifying agents are conventionally mineral or organic acids such as, for example, hydrochloric acid, tartaric acid, citric acid and phosphoric acid.

Among the buffers which may be mentioned, for example, is potassium dihydrogen phosphate/sodium hydroxide.

The composition applied to the hair can be in various forms, such as in the form of a liquid, cream or gel or in any other form which is suitable for dyeing keratin fibres. In particular, it can be packaged under pressure in an aerosol can in the presence of a propellant and can form a mousse.

In accordance with the present invention, the process for dyeing keratin fibres, in particular human keratin fibres such as the hair, is essentially characterized in that a component (A) consisting of a composition containing, in a medium which is suitable for dyeing, at least one heterocyclic cationic amine as defined above, and a component (B) consisting of a composition containing, in a medium which is suitable for dyeing, at least one compound chosen from an aldehyde, a ketone, a quinone and a diiminoisoindoline or 3-aminoisoindolone derivative such as, for example, one of the those defined above, is applied to the said fibres so as to allow the development of a coloration on the said keratin fibres.

In one preferred embodiment of the process of the invention, the components (A) and (B) are mixed together just before use, and the resulting composition is then applied immediately to the keratin fibres, and is left to act on them for 1 to 60 minutes and preferably from 1 to 30 minutes; the keratin fibres then being rinsed, washed with shampoo, rinsed again and then dried.

Another process of the present invention consists essentially in applying component (A) to the keratin fibres, followed or preceded by application of component (B) to the said fibres, in leaving each component to act for 1 to 60 minutes and preferably from 1 to 30 minutes, and optionally in rinsing with water between each application; the keratin fibres then being rinsed, washed with shampoo, rinsed again and then dried.

A subject of the invention is also an agent for dyeing keratin fibres, in particular human hair, characterized in that it consists of components (A) and (B) stored separately, as defined above.

Components (A) and (B) are intended either to be mixed together immediately before use or to be applied successively to the fibres to be treated.

According to one embodiment, the various components (A) and (B) can be packaged in a multi-compartment device also known as a "dyeing kit" comprising all the components intended to be applied for the same dyeing operation on keratin fibres, in particular human keratin fibres such as the hair, in successive applications with or without premixing.

Such devices can comprise a first compartment containing component (A) containing the heterocyclic cationic amine and a second compartment containing component (B) containing the compound chosen from an aldehyde, a ketone, a quinone and a diiminoisoindoline or 3-aminoisoindolone derivative.

Another variant can also consist in storing component (A) or component (B) in an anhydrous solvent medium and in providing a third compartment containing a cosmetically acceptable aqueous medium which is suitable for dyeing. In this case, the contents of the third compartment are mixed, immediately before use, into one or other or both of the compartments containing the anhydrous components (A) and (B), or alternatively the three compartments are mixed together before use.

Concrete examples illustrating the invention will now be given.

EXAMPLE 1

The dye composition below was prepared just before use:

1H-indole-2,3-dione ($3 \times 10^{-3}$ mol) 0.441 g

3-[3-(4-aminophenylamino)propyl]-1-methyl-3H-imidazolium chloride hydrochloride ($3 \times 10^{-3}$ mol) 1.02 g ethyl alcohol 20 g triethanolamine qs pH 7 water qs 100 g

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| bright brown-red | bright brown-red | bright brown-red |

These colorations withstand shampoo-washing particularly well.

EXAMPLE 2

The dye composition below was prepared just before use:

1H-indole-2,3-dione ($3 \times 10^{-3}$ mol) 0.441 g

3-[3-(4-aminophenylamino)propyl]-1-methyl-3H-imidazolium chloride hydrochloride ($3 \times 10^{-3}$ mol) 1.02 g ethyl alcohol 20 g triethanolamine qs pH 4 water qs 100 g

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent waved grey hair |
|---|---|---|
| rosewood | light red-copper | light red-copper |

These colorations withstand shampoo-washing particularly well.

EXAMPLE 3

The dye composition below was prepared just before use:

1H-indole-2,3-dione ($3 \times 10^{-3}$ mol) 0.441 g 1,3-bis{3-[3-(4-aminophenylamino)propyl]-3H-imidazol-1-ium}propane chloride hydrochloride ($3 \times 10^{-3}$ mol) 2.07 g ethyl alcohol 20 g triethanolamine qs pH 7 water qs 100 g

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| magenta | very bright magenta | very bright magenta |

These colorations withstand shampoo-washing particularly well.

EXAMPLE 4

The dye composition below was prepared just before use:

1H-indole-2,3-dione ($3 \times 10^{-3}$ mol) 0.441 g 1,3-bis{3-[3-(4-aminophenylamino)propyl]-3H-imidazol-1-ium}propane chloride hydrochloride ($3 \times 10^{-3}$ mol) 2.07 g ethyl alcohol 20 g triethanolamine qs pH 4 water qs 100 g

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| very bright rosewood | flaming red-copper | bright red-copper |

These colorations are fast in particular with respect to shampooing.

EXAMPLE 5

The dye composition below was prepared just before use:

1H-indole-2,3-dione ($3 \times 10^{-3}$ mol) 0.441 g

1-[3-(2,5-diaminophenoxy)propyl]-3-methyl-3H-imidazol-1-ium chloride hydrochloride ($3 \times 10^{-3}$ mol) 1.07 g ethyl alcohol 20 g triethanolamine qs pH 7 water qs 100 g

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent waved grey hair |
|---|---|---|
| light red-brown | bright red-brown | bright red-brown |

These colorations are fast in particular with respect to shampooing.

EXAMPLE 6

The dye composition below was prepared just before use:

1H-indole-2,3-dione ($3 \times 10^{-3}$ mol) 0.441 g

1-[3-(2,5-diaminophenoxy)propyl]-3-methyl-3H-imidazol-1-ium chloride hydrochloride ($3 \times 10^{-3}$ mol) 1.07 g ethyl alcohol 20 g triethanolamine qs pH 4 water qs 100 g

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| pinkish blond | light chesnut | red-brown |

These colorations are fast in particular with respect to shampooing.

EXAMPLE 7

The dye composition below was prepared just before use:

1-methyl-1H-indole-2,3-dione ($3 \times 10^{-3}$ mol) 0.483 g

3-[3-(4-aminophenylamino)propyl]-1-methyl-3H-imidazolium chloride hydrochloride ($3 \times 10^{-3}$ mol) 1.02 g ethyl alcohol 20 g
triethanolamine qs pH 7
water qs 100 g The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| dark red | dark red with violet glint | dark red with violet glint |

These colorations are fast in particular with respect to shampooing.

EXAMPLE 8

The dye composition below was prepared just before use:
1-methyl-1H-indole-2,3-dione ($3\times10^{-3}$ mol) 0.483 g
3-[3-(4-aminophenylamino)propyl]-1-methyl-3H-imidazolium chloride hydrochloride ($3\times10^{-3}$ mol) 1.02 g
ethyl alcohol 20 g
triethanolamine qs pH 4
water qs 100 g The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent waved grey hair |
|---|---|---|
| pinkish red | red-copper | coppery-red |

These colorations are fast in particular with respect to shampooing.

EXAMPLE 9

The dye composition below was prepared just before use:
1-methyl-1H-indole-2,3-dione ($3\times10^{-3}$ mol) 0.483 g
1,3-bis{3-[3-(4-aminophenylamino)propyl]-3H-imidazol-1-ium}propane chloride hydrochloride ($3\times10^{-3}$ mol) 2.07 g
ethyl alcohol 20 g
triethanolamine qs pH 7
water qs 100 g The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| prune | bright prune | bright prune |

These colorations are fast in particular with respect to shampooing.

EXAMPLE 10

The dye composition below was prepared just before use:
1-methyl-1H-indole-2,3-dione ($3\times10^{-3}$ mol) 0.483 g
1,3-bis{3-[3-(4-aminophenylamino)propyl]-3H-imidazol-1-ium}propane chloride hydrochloride ($3\times10^{-3}$ mol) 2.07 g
ethyl alcohol 20 g
triethanolamine qs pH 4
water qs 100 g The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| red-brown | bright red-brown | bright red-brown |

These colorations are fast in particular with respect to shampooing.

In the claims:

1. A process for dyeing at least one keratin fiber comprising applying to said at least one keratin fiber a composition comprising:
   (a) at least one compound chosen from aldehydes; ketones; quinones; diiminoisoindoline derivatives; and 3-aminoisoindolone derivatives; and
   (b) at least one heterocyclic cationic amine chosen from amines having formula (I) and the cosmetically acceptable salts thereof:

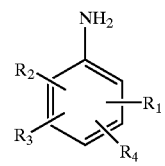

(I)

wherein
$R_1$, $R_2$, $R_3$ and $R_4$, which may be identical or different, are chosen from hydrogen; halogens; —$NH_2$ groups; —OH groups; —Z groups; —COZ groups; —COOZ groups; alkylcarbonyl groups; aminoalkylcarbonyl groups; N-alkylaminoalkylcarbonyl groups; N,N-dialkylaminoalkylcarbonyl groups; aminoalkylcarbonylalkyl groups; N-alkylaminoalkylcarbonylalkyl groups; N,N-dialkylaminoalkylcarbonylalkyl groups; carboxyl groups; alkylcarboxyl groups; alkylsulphonyl groups; aminosulphonyl groups; N-alkylaminosulphonyl groups; N,N-dialkylaminosulphonyl groups; aminosulphonylalkyl groups; N-alkylaminosulphonylalkyl groups; N,N-dialkylaminosulphonylalkyl groups; carbamyl groups; N-alkylcarbamyl groups; N,N-dialkylcarbamyl groups; carbamylalkyl groups; N-alkylcarbamylalkyl group; N,N-dialkylcarbamylalkyl groups; alkyl groups; monohydroxyalkyl groups; polyhydroxyalkyl groups; alkoxyalkyl groups; trifluoroalkyl groups; cyano groups; —$OR_l$ groups; —$SR_l$ groups; —$OR_lZ$ groups; —$SR_lZ$ groups; and amino groups protected with at least one group chosen from alkylcarboxyl groups, trifluoroalkylcarbonyl groups, aminoalkylcarbonyl groups, carbonyl groups, N-alkylaminoalkylcarbonyl groups, N,N-di-alkylaminoalkylcarbonyl groups, alkylcarboxyl groups, carbamyl groups, N-alkylcarbamyl groups, N,N-dialkylcarbamyl groups, alkylsulphonyl groups, aminosulphonyl groups, N-alkylaminosulphonyl groups, N,N-dialkylaminosulphonyl groups, thiocarbamyl groups, formyl groups, —COZ groups, and —COOZ groups;

wherein:

$R_1$, which may be identical or different, are each chosen from alkyl groups; monohydroxyalkyl groups; polyhydroxyalkyl groups; —Z groups; alkoxyalkyl groups; aryl groups; benzyl groups; carboxyalkyl groups; alkylcarboxyalkyl groups; cyanoalkyl groups; carbamylalkyl groups; N-alkylcarbamylalkyl groups; N,N-dialkylcarbamylalkyl groups; trifluoroalkyl groups; aminosulphonylalkyl groups; N-alkylaminosulphonylalkyl groups; N,N-dialkylaminosulphonylalkyl groups; alkylsulphinylalkyl groups; arkylsulphonylalkyl groups; alkylcarbonylalkyl groups; aminoalkyl groups; and aminoalkyl groups in which said amine is substituted with at least one group chosen from alkyl groups, monohydroxyalkyl groups, polyhydroxyalkyl groups, alkylcarbonyl groups, formyl groups, trifluoroalkylcarbonyl groups, alkylcarboxyl groups, carbamyl groups, N-alkylcarbamyl groups, N,N-dialkylcarbamyl groups, thiocarbamyl groups, alkylsulphonyl groups, —Z groups, —COZ groups, and and —COOZ groups;

Z, which may be identical or different, are each chosen from groups having formula (II) and groups having formula (III):

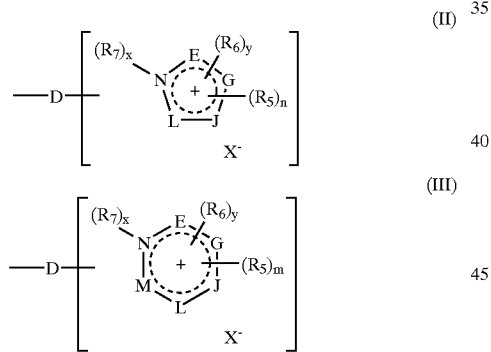

wherein

D, which may be identical or different, are each chosen from linear divalent alkyl chains and branched divalent alkyl chains, which chains may comprise from 1 to 14 carbon atoms, may be interrupted by at least one heteroatom, may be substituted with at least one group chosen from hydroxyl and $C_1$–$C_6$ alkoxy groups, and may comprise at least one ketone group;

E, G, J, L and M, which may be identical or different, are each chosen from carbon atoms; oxygen atoms; sulphur atoms; and nitrogen atoms;

n is an integer ranging from 0 to 4;

m is an integer ranging from 0 to 5;

$R_5$, which may be identical or different, are each chosen from a bond to D; —Z groups; halogens; hydroxyl groups; $C_1$–$C_6$ alkyl groups; $C_1$–$C_6$ mono hydroxyalkyl groups; $C_2$–$C_6$ polyhydroxyalkyl groups; nitro groups; cyano groups; cyano ($C_1$–$C_6$)alkyl groups; $C_1$–$C_6$ alkoxy groups, tri($C_1$–$C_6$)alkylsilane($C_1$–$C_6$) alkyl groups; amido groups; aldehyde groups; carboxyl groups; ($C_1$–$C_6$)alkylcarbonyl groups; thio groups; $C_1$–$C_6$ thioalkyl groups; $C_1$–$C_6$alkylthio groups; amino groups; amino groups protected with at least one group chosen from ($C_1$–$C_6$)alkylcarbonyl groups, carbamyl groups, with $C_1$–$C_6$ alkylsuphonyl groups; and groups chosen from NHR" groups and NR"R''' groups in which R" and R''', which may be identical or different, are each chosen from $C_1$–$C_6$ alkyl groups, $C_{1-C6}$ monohydroxyalkyl groups, and $C_2$–$C_6$polyhydroxyalkyl groups;

$R_6$ is chosen from a bond to D; $C_1$–$C_6$ alkyl groups; $C_1$–$C_6$ monohydroxyalkyl groups; $C_2$–$C_6$ polyhydroxyalkyl groups; cyano($C_1$–$C_6$)alkyl groups; tri ($C_1$–$C_6$)alkylsilane-($C_1$–$C_6$)alkyl groups; ($C_1$–$C_6$) alkoxy($C_1$–$C_6$)alkyl groups; carbamyl($C_1$–$C_6$)alkyl groups; ($C_1$–$C_6$)alkylcarboxy($C_1$–$C_6$)alkyl groups; benzyl groups; and Z groups;

$R_7$ is chosen from a bond to D; $C_1$–$C_6$ alkyl groups; $C_1$–$C_6$ monohydroxyalkyl groups; $C_2$–$C_6$ polyhydroxyalkyl groups; aryl groups; benzyl groups; $C_1$–$C_6$ aminoalkyl groups; $C_1$–$C_6$ aminoalkyl groups wherein said amine is protected with at least one group chosen from ($C_1$–$C_6$)alkylcarbonyl groups, carbamyl groups, and $C_1$–$C_6$ alkylsulphonyl groups; carboxy($C_1$–$C_6$) alkyl groups; cyano($C_1$–$C_6$)alkyl groups; carbamyl ($C_1$–$C_6$)alkyl groups; $C_1$–$C_6$ trifluoroalkyl groups; tri ($C_1$–$C_6$)alkylsilane($C_1$–$C_6$)alkyl groups; $C_1$–$C_6$ sulphonamidoalkyl groups; ($C_1$–$C_6$) alkylcarboxy ($C_1$–$C_6$)alkyl groups; ($C_1$–$C_6$)alkylsulphinyl($C_1$–$C_6$) alkyl groups; ($C_1$–$C_6$)alkylsulphonyl($C_1$–$C_6$)alkyl groups; ($C_1$–$C_6$)alkylketo($C_1$–$C_6$)alkyl groups; N—($C_1$–$C_6$)alkylcarbamyl($C_1$–$C_6$)alkyl groups; and N—($C_1$–$C_6$)alkylsulphonamido($C_1$–$C_6$)alkyl groups;

x and y, which may be identical or different, are integers chosen from 0 and 1, with the proviso that, in said groups having formula (II):

when x=0, D is attached to the nitrogen atom of the ring;

when x=1, D is attached to at least one of E, G, J and L;

when y=1:
E, G, J and L each simultaneously represent a carbon atom, and $R_6$ is bonded to the nitrogen atom of the ring of formula (II); or at least one of E, G, J and L is chosen from a nitrogen atom to which $R_6$ is bonded;

and with the proviso that, in said groups having formula (III);

when x=0, D is attached to the nitrogen atom of the ring;

when x=1, D is attached to at least one of E, G, J, L and M;

when y=1, at least one of E, G, J, L and M is chosen from divalent atoms and $R_6$ is bonded to the at least one nitrogen atom of the ring of formula (III);

$X^\ominus$, which may be identical or different, are each chosen from monovalent anions and divalent anions;

and with the proviso that in said amine of formula (I), at least one of $R_1$, $R_2$, $R_3$, and $R_4$ comprises at least one Z group, wherein a coloration of said at least one keratin fiber is achieved without an oxidizing agent.

2. A process according to claim 1, wherein said at least one keratin fiber is a human keratin fiber.

3. A process according to claim 2, wherein said human keratin fiber is hair.

4. A process according to claim 2, wherein said at least one heteroatom is chosen from oxygen; sulphur; and nitrogen.

5. A process according to claim 2, wherein said monovalent anions and divalent anions are chosen from halogen; hydroxide anions; hydrogen sulphate anions; and alkyl sulphate anions.

6. A process according to claim 5, wherein said halogens are chosen from chlorine; bromine; fluorine; and iodine.

7. A process according to claim 5, wherein said alkyl sulphate anions are chosen from methyl sulphate and ethyl sulphate.

8. A process according to claim 1, wherein said at least one compound is chosen from aldehydes having the formula (IV) and the cosmetically acceptable salts thereof:

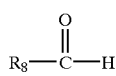
(IV)

in which $R_8$ is chosen from groups having formula (IV A):

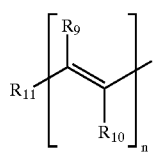
(IV A)

in which:

$R_9$ and $R_{10}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_9$ and $R_{10}$, which may be identical or different, may also form, together with the atoms to which they are attached, at least one ring, optionally substituted, chosen from aryl rings; 5-membered heterocyclic rings; and 6-membered heterocyclic rings;

n is an integer ranging from 0 to 3; and $R_{11}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted, alkylaryl groups, optionally substituted; 5-membered heterocyclic groups, optionally substituted; and 6-membered heterocyclic groups, optionally substituted.

9. A process according to claim 1, wherein said at least one compound is chosen from ketones having formula (V), ketones having formula (VI), and the cosmetically acceptable salts thereof:

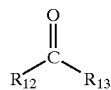
(V)

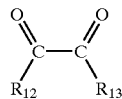
(VI)

in which:

$R_{12}$ is chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_{13}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and $R_{12}$ and $R_{13}$ may also form, together with the atoms to which they are attached, at least one ring chosen from 5-membered aryl rings; 6-membered aryl rings; and heterocyclic rings, it being possible for said at least one ring itself to be attached to at least one additional ring, optionally substituted, which may be identical or different from said at least one ring, wherein said at least one additional ring is chosen from 5-membered aryl rings; 6-membered aryl rings; and heterocyclic rings.

10. A process according to claim 9, wherein said heterocyclic rings comprise at least one heteroatom chosen from N and S.

11. A process according to claim 1, wherein said at least one compound is chosen from quinones having formula (VII), quinones having formula (VIII), and the cosmetically acceptable salts thereof:

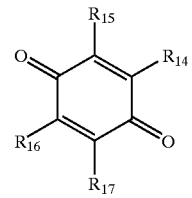
(VII)

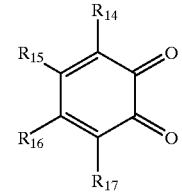
(VIII)

in which:

$R_{14}$ is chosen from hydrogen; halogens; sulphonic groups; and alkoxy groups;

$R_{15}$, $R_{16}$ and $R_{17}$, which may be identical or different, are each chosen from hydrogen; halogens; hydroxyl groups; alkyl groups; monohydroxyalkyl groups; polyhydroxyalkyl groups; alkylhydroxyalkyl groups; alkylsulphonyl groups; carboxyalkyl groups; aminoalkyl groups; alkylaminoalkyl groups; (dihydroxy) alkylaminoalkyl groups; alkyl-NR'R" groups wherein R' and R", which may be identical or different, are each chosen from alkyl groups, or R' and R" may also form, together with the nitrogen atom to which they are attached, at least one ring chosen from aryl rings, 5-membered heterocycles, and 6-membered heterocycles; aryl groups; and amino groups, optionally substituted with at least one group chosen from alkyl groups and hydroxyalkyl groups; and at least one of $R_{14}$ and $R_{15}$, $R_{15}$ and $R_{16}$, and $R_{16}$ and $R_{17}$, may also form, together with the atoms to which they are attached, at least one ring, optionally substituted, chosen from aryl rings; 5-membered heterocycles; and 6-membered heterocycles.

12. A process according to claim 1, wherein said at least one compound is chosen from diaminoisoindolines having formula (IX), 3-aminoisoindolone derivatives having formula (IX), and the cosmetically acceptable salts thereof;

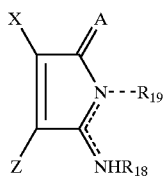 (IX)

in which:

$R_{18}$ and $R_{19}$, which may be identical or different, are each chosen from hydrogen; alkyl groups; monohydroxyalkyl groups; polyhydroxyalkyl groups; alkylhydroxyalkyl groups; aminoalkyl groups; alkylaminoalkyl groups; (dihydroxy)alkylaminoalkyl groups; and alkyl-NR'R" groups wherein R' and R", which may be identical or different, are each chosen from alkyl groups, or may also form, together with the nitrogen atom to which they are attached, at least one ring chosen from aryl rings; 5-membered heterocycles; and 6-membered heterocycles;

A is chosen from oxygen and NH; and

X and Z form, together with the atoms to which they are attached, at least one ring, optionally substituted, chosen from aryl rings; 5-membered heterocycles; and 6-membered heterocycles.

13. A process according to claim 1, wherein said groups having formula (II) are chosen from pyrrole rings; imidazole rings; pyrazole rings; oxazole rings; thiazole rings; and trizole rings.

14. A process according to claim 1, wherein said groups having formula (III) are chosen from pyridine rings; pyrimidine rings; pyrazine rings; oxazine rings; and triazine rings.

15. A process according to claim 1, wherein said at least one heterocyclic cationic amine is chosen from amines having formula (I), wherein said amines having formula (I) are chosen from:

1-[3-((2,4-diaminophenoxy)propyl]-3-methyl-3H-imidazol-1-ium chloride;

1-[(3-hydroxy-4-methylphenylcarbamoyl)methyl]-3-methyl-3H-imidazole-1-ium chloride;

3-ethyl-1-[(3-hydroxyphenylcarbamoyl)methyl]-3H-imidazol-1-ium chloride;

1-[(3-hydroxy-2,4-dimethylphenylcarbamoyl)methyl]-3-methyl-3H-imidazol-1-ium chloride;

1-[(4-chloro-3-hydroxyphenylcarbamoyl)methyl]-3-ethyl-3H-imidazol-1-ium chloride;

1-[(3-hydroxy-4-methoxyphenylcarbamoyl)methyl]-3-methyl-3H-imidazol-1-ium chloride;

1-[(3-hydroxy-4-methylphenylcarbamoyl)methyl]-2-methyl-2H-pyrazol-1-ium chloride;

1-[2-(3-hydroxy-4-methylphenylamino)ethyl]-3-methyl-3H-imidazol-1-ium bromide;

1-[2-(3-hydroxy-4-methylphenylcarbamoyloxy)ethyl]-2,3-dimethyl-3H-imidazol-1-ium chloride;

1-{[3-amino-4-(3-(3-methyl-3H-imidazol-1-ium)propoxy)-phenylcarbamoyl]methyl}-3-methyl-3H-imidazol-1-ium dichloride;

3-(3-trimethylammonium-2-hydroxypropyl)-1-[(3-hydroxy-4-methylphenylcarbamoyl)methyl]-3H-imidazol-1-ium dichloride;

1-{[2-(2,4-diaminophenoxy)ethylcarbamoyl]methyl}-3-methyl-3H-imidazol-1-ium chloride;

1-[(2,4-dihydroxyphenylcarbamoyl)methyl]-3-methyl-3H-imidazol-1-ium chloride;

N,N-bis[2-(3-methyl-3H-imidazol-1-ium)ethyl]benzene-1,3-diamine dichloride;

1-{3-[4-amino-2-(2-triethylammoniumacetylamino)phenoxy]propyl}-3-methyl-3H-imidazol-1-ium dichloride;

1-(3-{4-amino-2-[2-(3methyl-3H-imidazol-1-ium)-acetylamino]phenoxy}propyl)-1,4-dimethylpiperazin-1-ium dichloride;

1-[2-(2,4-dihydroxyphenyl)-2-oxoethyl]-3-methyl-3H-imidazol-1-ium chloride;

1-[2-(2,4-diaminophenyl)ethyl]-3-methyl-3H-imidazol-1-ium chloride;

1,4-bis-1-{3-[3-(2,4-diaminophenoxy)propyl]-3H-imidazol-1-ium}butane dichloride monohydrate;

1,3-bis[3-(2,4-diaminophenoxy)propyl]-3H-imidazol-1-ium chloride;

3-[3-(2,4-diaminophenoxy)propyl]-1-[(3-hydroxy-4-methylphenylcarbamoyl)methyl]-3H-imidazol-1-ium chloride;

1,4-bis-{3-[(3-hydroxy-4-methylphenylcarbamoyl)methyl]-3H-imidazol-1-ium}butane dichloride;

1,4-bis{3-[2-(2,4-diaminophenyl)ethyl]-3H-imidazol-1-ium}butane dichloride;

1,4-bis{3-[2-(3-hydroxy-4-methylphenylamino)ethyl]-3H-imidazol-1-ium}butane dibromide;

1,4-bis{3-[(2,4-dihydroxyphenylcarbamoyl)methyl]-3H-imidazol-1-ium}butane dichloride;

3-[3-(2,4-diaminophenoxy)propyl]1-[(2,4-dihydroxyphenylcarbamoyl)methyl]-3H-imidazol-1-ium chloride;

3-[3-(2-aminophenylamino)propyl]-1-methyl-3H-imidazol-1-ium monochloride;

3-[2-(2-aminophenylamino)ethyl]-1-methyl-3H-imidazol-1-ium monochloride;

4-[2-(1-methyl-3H-imidazol-1-ium)ethoxy-N2-[2-(1methyl-3H-imidazol-1-ium)ethyl]benzene-1,2-diamine dichloride;

3-[2-(2-amino-4-methylphenylamino)ethyl]-1-ethyl-3H-imidazol-1-ium monochloride;

3-[3-(2-aminophenylamino)propyl]-1-(3-trimethylammonium-2-hydroxypropyl)-3H-imidazol-1-ium dichloride;

3-[3-(2-aminophenylamino)propyl]-1-(2-hydroxyethyl)-3H-imidazol-1-ium monobromide;

3-{[2-(2-aminophenylamino)ethylcarbamoyl]methyl}-1-methyl-3H-imidazol-1-ium monochloride;

1-[2-(2-amino-4-chlorophenylamino)ethyl]pyridinium monochloride;

3-[2-(2-amino-5-methoxyphenylamino)ethyl]-1-methyl-3H-imidazol-1-ium monochloride;

3-[2-(2-amino-5-methylsulphanylphenylamino)ethyl]-1-methyl-3H-imidazol-1-ium monochloride;

1-[2-(4-aminophenylamino)ethyl]-3-methyl-3H-imidazol-1-ium bromide;

1-[3-(2,3-diaminophenoxy)propyl]-3-methyl-3H-imidazol-1-ium chloride;

3-[3-(4-aminophenylamino)propyl]-1-methyl-3H-imidazol-1-ium chloride;

3-[3-(4-amino-3-methylphenylamino)propyl]-1-methyl-3H-imidazol-1-ium chloride;

3-[3-(4-amino-2-methylphenylamino)propyl]-1-methyl-3H-imidazol-1-ium chloride;

3-[3-(4-amino-2-fluorophenylamino)propyl]-1-methyl-3H-imidazol-1-ium chloride monohydrate;

3-[3-(4-amino-2-cyanophenylamino)propyl]-1-methyl-3H-imidazol-1-ium chloride;

1-[2-(4-amino-2-methoxyphenylamino)ethyl]-3-methyl-3H-imidazol-1-ium chloride;

and the acid addition salts thereof.

16. A process according to claim 1, wherein said at least one heterocyclic cationic amine is chosen from amines having formula (I), wherein said amines having formula (I) are chosen from:

1-(5-amino-2-hydroxybenzyl)-3-methyl-3H-imidazol-1-ium chloride;

1-(5-amino-2-hydroxybenzyl)-2-methyl-2H-pyrazol-1-ium chloride;

1[2-(2,5-diaminophenyl)ethyl]-3-methyl-3H-imidazol-1-ium chloride;

1,3-bis-1-{3-{3'-[(4"-amino-3"-methylanilino)-N-propyl]}-3H-imidazol-1-ium}propane dichloride;

1,3-bis-1-{3-{3'-[(4"-amino-2"-methylanilino)-N-propyl]}-3H-imidazol-1-ium}propane dichloride monohydrate diethanol;

1,3-bis-1-{3-{3'-[(4"-aminoanilino)-N-propyl]}-3H-imidazol-1-ium}propane dichloride monohydrate ethanol;

1,3-bis-1-{3-{3'-[(4"-amino-2"-methylanilino)-N-propyl]}-3H-imidazol-1-ium}-2-propanol dichloride monohydrate;

1,4-bis-1-{3-[3-(2,5-diaminophenoxy)propyl]-3H-imidazol-1-ium}butane dichloride dihydrate;

1,3-bis[3-(2,5-diaminophenoxy)propyl]-3H-imidazol-1-ium monochloride monohydrate;

1,4-bis-1-[3-(5-amino-2-hydroxybenzyl)-3H-imidazol-1-ium]butane dichloride monohydrate;

1,3-bis{3-{3-[(2-aminoanilino)-N-propyl]}-3H-imidazol-1-ium}propane dibromide;

1,4-bis{3-{2-[2-aminoanilino)-N-ethyl]}-3H-imidazol-1-ium}butane dichloride;

1-[2-(2-aminoanilino)ethyl]-3-[3-(2-aminoanilino)propyl]-3H-imidazol-1-ium monochloride;

and acid addition salts thereof.

17. A process according to claim 1, wherein said at least one compound is chosen from benzaldehyde; 2-monohydroxybenzaldehyde; 3-monohydroxybenzaldehyde; 4-monohydroxybenzaldehyde; 2-monomethoxybenzaldehyde; 3-monomethoxybenzaldehyde; 4-monomethoxybenzaldehyde; 2-monomethylbenzaldehyde; 3-monomethylbenzaldehyde; 4-monomethylbenzaldehyde; (2,3)-dihydroxybenzaldhyde; (2,4)-dihydroxybenzaldehyde; (2,5)-dihydroxybenzaldehyde; (2,6)-dihydroxybenazldehyde; (3,5)-dihydroxybenzaldehyde; (2,3)-dimethoxybenzaldehyde; (2,4)-dimethoxybenzaldehyde; (2,5)-dimethoxybenzaldehyde; (2,6)-dimethoxybenzaldehyde; (3,5)-dimethoxybenzaldehyde; vanillin; isovanillin; syringaldehyde; orthophthalaldehyde; isophthalaldehyde; terephthalaldehyde; (2,3)-dimethylbenzaldehyde; (2,4)-dimethylbenzaldehyde; (2,5)-dimethylbenzaldehyde; (2,6)-dimethylbenzaldehyde; (3,5)-dimethylbenzaldehyde; (4-isopropylbenzaldehyde; 4-dimethylaminobenzaldehyde; 4-diethylaminobenzaldehyde; piperonal; (2,6)-dimethyl-4-hydroxybenzaldehyde; (3,5)-dimethyl-4-hydroxybenzaldehyde; 2-mononitrobenzaldehyde; 3-mononitrobenzaldehyde; 4-mononitrobenzaldehyde; 2-hydroxy-3-methoxybenzaldehyde; 2-hydroxy-4-methoxybenzaldehyde; 2-hydroxy-5-methoxybenzaldehyde; 2-hydroxy-6-methoxybenzaldehyde; 4-methylthiobenzaldehyde; (2,3,4)-trihydroxybenzaldehyde; (2,4,6)-trihydroxybenzaldehyde; (3,4,5)-tri-hydroxybenzaldehyde; (2,4,5)-trihydroxybenzaldehyde; methyl 2-formyl benzoate; methyl 3-formyl benzoate; methyl 4-formyl benzoate; 2-mono(2-hydroxyethoxy)benzaldehyde; 3-mono(2-hydroxyethoxy)benzaldehyde; 4-mono(2-hydroxyethoxy)benzaldehyde; 4-nitro-3-hydroxybenzaldehyde; 3-nitro-4-hydroxybenzaldehyde; 2-nitro-4-hydroxybenzaldehyde; 3-nitro-2-hydroxy-benzaldehyde; 2-monotrifluorobenzaldehyde; 3-monotrifluorobenzaldehyde; 4-monotrifluorobenzaldehyde; 2,3-dihydroxy-4-methoxybenzaldehyde; 3,4-dihydroxy-5-methoxybenzaldehyde; 3,5-dihydroxy-4-methoxybenzaldehyde; 3-methoxy-2-nitrobenzaldehyde; 4-methoxy-3-nitrobenzaldehyde; (2,3,4-trimethoxybenzaldehyde; (2,4,6)-trimethoxybenzaldehyde; (3,4,5)-trimethoxybenzaldehyde; (2,4,5-trimethoxybanzaldehyde; 5-nitrovanillin; (2,4) dinitrobenzaldehyde; (2,6)-dinitrobenzaldehyde; pentaethylbenzaldehyde; 4-methylsulphonylbenzaldhyde; 2-monoformylphenoxyacetic acid; 3-monoformylphenoxyacetic acid; 4-monoformylphenoxyacetic acid; 4-diethyl-aminosalicylaldehyde; 4-(3-dimethylaminopropoxy)benzaldehyde; 2,3-dihydrobenzo(b)furan-5-carboxyaldehyde; 1-naphthaldehyde; 2-naphthaldehyde; 6-carboxyaldehyde-1,4-benzodioxane; 5-carboxaldehyde-1,4-benzodioxane; 2-monohydroxy-1-naphthaldehyde; 4-monohydroxy-1-naphthaldehyde; 1-monohydroxy-2-naphthaldehyde; 1-(4-formylphenyl)-imidazole; 4-pyrrolidinobenzaldehyde; 2-monomethoxy-1-naphthaldehyde; 4-monomethoxy-1-naphthaldehyde; 2,3-dimethylchroman-6-carboxaldehyde; 2,3,6,7-tetrahydro-1H,5H-pyrido(3,2,1-lJ)quinoline-9-carbaldehyde; 4-dimethyl amino-1-naphthaldehyde; 9-anthraldehyde; 3-nitro-4-pyrrolidinobenzaldehyde; 3-nitro-4-piperidinobenzaldehyde; 3-nitro-4-morpholinobenzaldehyde; pyridine-2-monocarboxaldhyde; pyridine-3-monocarboxaldehyde; pyridine-4-monocarboxaldehyde; 2,6-pyridinodicarboxaldehyde; 5-formyl-6-methyluracil; pyridoxal; quinoline-2-monocarboxaldehyde; quinoline-3-monocarboxaldehyde; quinoline-4-monocarboxaldehyde; 8-hydroxyquinoline-2-carboxaldehyde; 2-furaldehyde; 3-furaldehyde; 2-thienylcarboxaldehyde; 3-thienylcarboxaldehyde;

2-imidazocarboxaldhyde; 3-imidazocarboxaldehyde; 2-pyrrolecarboxaldehyde; 5-nitro-2-furaldehyde; 5-(dimethylamino)-2-furaldehyde; 2,5-thiophenedicarboxaldehyde; 2,3-thiophenedicarboxaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4-monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

18. A process according to claim 1, wherein said at least one compound is chosen from 2,3-indolinedione; 2,3-butanedione; 2,3-pentanedione; (2,3-hexanedione; (3,4-hexanedione; 1-phenyl-1,2-propanedione; benzil; furil; 2,2'-pyridil; nitrobenzil; anisil; 3,3'-dimethoxybenzil; 4,4'-bis (dimethylamino)benzil; camphoroquinone; cyclohexane-1, 2-dione; isatin; N-methylisatin; 4-mono-methylsatin; 5-monomethylisatin; 6-monomethylisatin; 7-monomethylisatin; (4,5)-dimethylisatin; (4,7) dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4, 5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxyoxindole; 5-monochlorooxindole; and 6-monochlorooxindole.

19. A process according to claim 1, wherein said at least one compound is chosen from 1,4-naphthoquinone, spinulosin; atromentin; aurentiogliocladin; 2,5-dihydroxy-6-methylbenzoquinone; 2-hydroxy-3-methyl-6-methoxybenzoquinone; 2,5-dihydroxy-3,6-diphenylbenzoquinone; 2,3-dimethyl-5-hydroxy-6-methoxybenzoquinone; 2,5-dihydroxy-6-isopropylbenzoquinone; lawsone; juglone; fafioline; naphthazarine; naphthopurpurine; lapachol; plumbagin; chloroplumbagin; droserone; shikonine; 2-hydroxy-3-methyl-1,4-naphthoquinone, 3,5-dihydroxy-1,4-naphthoquinone; 2,5-dihydroxy-1,4-naphthoquinone; 2-methoxy-5-hydroxy-1,4-naphthoquinone; 3-methoxy-5-hydroxy-1,4-naphthoquinone; (1,4)-naphthoquinone; (1,2)-naphthoquinone; 4,5-dimethoxy-1,2-benzoquinone; phenanthrenequinone; and (1,2)-naphtho quinone-4-sulphonic acid.

20. A process according to claim 1, wherein said at least one compound is chosen from 3-imino-3H-isoindolylamine; 3-imino-4-methyl-3H-isoindol-1-ylamine; 3-imino-4-tert-butyl-3H-isoindol-1-ylamine; 3-imino-7-nitro-3H-isoindol-1-ylamine; 3-amino-1-imino-1H-isoindol-4-ol; 3-imino-7-isopropoxy-3H-isoindol-1-ylamine; 3-imino-7-(2,2,2-trifluorethoxy)-3H-isoindol-1-ylamine; 3-imino-7-ethoxy-3H-isoindol-1-ylamine; 3-imino-7-butoxy-3H-isoindol-1-ylamine; 3-amino-1-imino-1H-isoindole-4-sulphonic acid; 3-imino-7-chloro-3H-isoindol-1-ylamine; 3-imino-5-methyl-3H-isoindol-1-ylamine; 3-imino-5-ethyl-3H-isoindol-1-ylamine; 3-imino-5-tert-butyl-3H-isoindol-1-ylamine; 3-imino-5-amino-3H-isoindol-1-ylamine; N-(1-amino-3-imino-3H-isoindol-5-yl)acetamide; 3-imino-5-nitro-3H-isoindol-1-ylamine; 3-imino-5fluoro-3H-isoindol-1-ylamine; 3-imino-5-chloro-3H-isoindol-1-ylamine; 3-imino-5-methylsulphanyl-3H-isoindol-1-ylamine; 3-imino-5-methoxy-3H-isoindol-1-ylamine; 3-imino-5-ethoxy-3H-isoindol-1-yl amine; 3-imino-5propoxy-3H-isoindol-1-ylamine; 3-imino-5-isopropoxy-3H-isoindol-1ylamine; 3-imino-5-butoxy-3H-isoindol-1-ylamine; 3-imino-5isobutoxy-3H-isoindol-1-ylamine; 3-imino-5-tert-butoxy-3H-isoindol-1-ylamine; 3-imino-5-(2,2,2-trifluoromethyl)-3H-isoindol-1-ylamine; 3-imino-5-(2,2,2-trifluroethoxy)-3-isoindol-1-ylamine; 3-imino-5-methane sulphonyl-3H-isoindol-1-ylamine; 3-imino-5,6-dimethyl-3H-isoindol-1-ylamine; 3-imino-5,6-diethyl-3H-isoindol-1-ylamine; 3-imino-5,6-dimethoxy-3H-isoindol-1-ylamine; 3-imino-5,6-diethoxy-3H-isoindol-1-ylamine; 3-imino-5,6-dibutoxy-3H-isoindol-1-ylamine; 3-imino-5,6-bis (trifluoromethyl)-3H-isoindol-1-ylamine; 3-imino-5,6-dichloro-3H-isoindol-1-ylamine; 5,6-bis(ethoxymethyl)3-imino-3H-isoindol-1-ylamine; 3-amino-1-imino-1H-isoindole-4,7-diol; 4,7-dichloro-3-imino-3H-isoindol-1-ylamine; 4,5,7-trichloro-3-imino-N6,N6-dimethyl-3H-isoindole-1,6-diamine; 4,5,6,7-tetrachloro-3-imino-3H-isoindol-1-ylamine; 4,5,6,7-tetrafluoro-3-imino-3H-isoindol-1-ylamine; 3-butylimino-3H-isoindol-1-ylamine; 2-(3-aminoisoindol-1-ylideneamino)ethanol; 3-(3-aminoisoindol-1-ylideneamino)-3-methylpentane-1,5-diol; N-(3-aminoisoindol-1-ylidene)guanidine; 7-imino-7H-pyrrolo[3,4-b]pyrid-5-ylamine; 7-imino-7H-pyrrolo[3,4-b] pyrazin-5-ylamine; 7-imino-2,3-dimethyl-7H-pyrrolo[3,4-b]pyrazin-5-ylamine; 7-imino-7H-[1,4]dithiino[2,3-c] pyrrol-5-ylamine; 7-imino-2,3-dimethyl-7H-[1,4]dithiino[2, 3-c]pyrrol-5-ylamine; 7-imino-2,3-dihydro-7H-[1,4] dithiino[2,3-c]pyrrol-5-ylamine; 3-aminoisoindol-1-one; 3-amino-7-methylisoindol-1-one; 3-amino-7-hydroxymethyl isoindol-1-one; 3-amino-7-chloroisoindol-1-one; 3-amino-4-chloroisoindol-1-one; 3amino-1-oxo-1H-isoindole-4-sulphonic acid; 3-amino-4-nitroisoindol-1-one; 3-amino-6-nitroisoindol-1-one; 3-amino-6-methyl-isoindol-1 1-one; 3-amino-6-methyl sulphanylisoindol-1-one; 3-amino-6-methoxyisoindol-1-one; 3-amino-5-chloroisoindol-1-one; 3-amino-5-fluoro isoindol-1-one; 3-amino-5-methoxyisoindol-1-one; 3-amino-5-nitroisoindol-1-one; ethyl 3-amino-1oxo-1H-isoindole-5-carboxylate; 3-amino-5,6-dichloroisoindol-1-one; 3-amino-5,6-dibromoisoindol-1one; 3-amino-4,7-dichloroisoindol-1-one; 3-amino-4,5,7-trichloroisoindol-1-one; 3-amino-4,5,6,7-tetrachloroisoindol-1-one; 3-amino-4,5,7-trichloro-6-methylsulphanylisoindol-1-one; 3-amino-4,5,6,7-tetrabromoisoindol-1-one; 3-amino-4,5,6,7-tetrafluoroisoindol-1-one; 3-methylamino isoindol-1-one; 3-ethylaminoisoindol-1-one; 3-propylaminoisoindol-1-one; 3-dimethylaminoisoindol-1-one; 7-ethylaminopyrrolo[3,4-b]pyrid-5-one; 7-aminopyrrolo[3,4-b]pyrid-5-one; 3-aminopyrrolo[3,4-c]pyrid-5-one; 3-amino-6-methylpyrrolo[3,4-c]pyrid-1-one; 5-aminopyrrolo[3,4-b] pyrid-7-one; 7-aminopyrrolo[3,4-b]pyrazin-5-one; 7-amino-2-methylpyrrolo[3,4-b]pyrazin-5-one; 7-amino-2,3-dimethylpyrrolo[3,4-b]pyrazin-5-one; 7-amino-2,3-dihydro-[1,4]dithiino[2,3-c]pyrrol-5-one; 3-imino-2-methyl-2,3-dihydroisoindol-1-one; 3-imino-2-ethyl-2,3-dihydroisoindol-1-one; 3-imino-2-propyl-2,3- dihydroisoindol-1-one; 2-hydroxymethyl-3-imino-2,3-dihydroisoindol-1-one; 2-(2-hydroxyethyl)-3-imino-2,3-dihydroisoindol-1-one; 2-1-imino-3-oxo-1,3-dihydroisoindol-2-yl)ethanesulphonic acid; 3-(1-imino-3-oxo-1,3-dihydroisoindol-2-yl)propionic acid; 2-(3-hydroxypropyl)-3-imino-2,3-dihydroisoindol-1-one and 5-imino-6-methyl-5,6-dihydropyrrolo[3,4-b]pyridin-7-one.

21. A process according to claim 8, wherein said salts are chosen from hydrochlorides; sulphates; hydrobromides; and tartrates.

22. A process according to claim 9, wherein said salts are chosen from hydrochlorides; sulphates; hydrobromides; and tartrates.

23. A process according to claim 11, wherein said salts are chosen from hydrochlorides; sulphates; hydrobromides; and tartrates.

24. A process according to claim 12, wherein said salts are chosen from hydrochlorides; sulphates; hydrobromides; and tartrates.

25. A process according to claim 15, wherein said salts are chosen from hydrochloride; sulphates; hydrobromides; and tartrates.

26. A process according to claim 16, wherein said salts are chosen from hydrochlorides; sulphates; hydrobromides; and tartrates.

27. A process according to claim 1, wherein said at least one compound is chosen from 1,4-dimethylaminobenzaldehyde and 4-dimethylaminonaphthaldehyde.

28. A composition of dyeing at least one keratin fiber, wherein said composition comprises:

(a) at least one heterocyclic cationic amine chosen from amines having formula (I) and the cosmetically acceptable salts thereof:

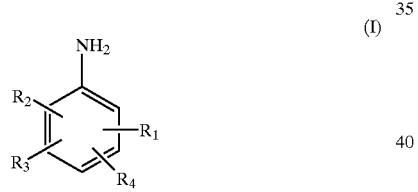

(I)

wherein:

$R_1$, $R_2$, $R_3$ and $R_4$, which may be identical or different, are each chosen from hydrogen; halogens; —$NH_2$ groups; —OH groups; —Z groups; —COZ groups; —COOZ groups; alkylcarbonyl groups; aminoalkylcarbonyl groups; NB alkylaminoalkylcarbonyl groups; N,N-dialkylaminoalkylcarbonyl groups; aminoalkylcarbonylalkyl groups, N-alkylaminoalkylcarbonylalkyl groups; N,N-dialkylaminoalkylcarbonylalkyl groups; carboxyl groups; alkylcarboxyl groups; alkylsulphonyl groups; aminosulphonyl groups; N-alkylaminosulphonyl groups; N,N-dialkylaminosulphonyl groups; aminosulphonylalkyl groups; N-alkylaminosulphonylalkyl groups; N,N-dialkylaminosulphonylalkyl groups; carbamyl groups; N-alkylcarbamyl groups; N,N-dialkylcarbamyl groups; carbamylalkyl groups; N-alkylcarbamylalkyl groups; N,N-dialkylcarbamylalkyl groups; alkyl groups; monohydroxyalkyl groups; polyhydroxyalkyl groups; alkoxyalkyl groups, trifluoroalkyl groups; cyano groups; —$OR_i$ groups; —$SR_i$ groups; —$OR_iZ$ groups; —$SR_iZ$ groups; and amino groups protected with at least one group chosen from alkylcarboxyl groups, trifluoroalkylcarbonyl groups, aminoalkylcarbonyl groups, carbonyl groups, N-alkylaminoalkylcarbonyl groups, N,N-dialkyl-aminoalkylcarbonyl groups, alkylcarboxyl groups, carbamyl groups, N-alkylcarbamyl groups, N,N-dialkylcarbamyl groups, alkylsulphonyl groups, aminosulphonyl groups, N-alkylaminosulphonyl groups, N,N-diakylamino sulphonyl groups, thiocarbamyl groups, formyl groups, —COZ groups, and —COOZ groups;

wherein $R_1$, which may be identical or different, are each chosen from alkyl groups; monohydroxalkyl groups; polyhydroxyalkyl groups; —Z groups; alkoxyalkyl groups; aryl groups; benzyl groups; carboxyalkyl groups; alkylcarboxyalkyl groups; cyanoalkyl groups; carbamylalkyl groups; N-alkylcarbamylalkyl groups; N,N-dialkylcarbamylalkyl groups, trifluoroalkyl groups; aminosulphonylalkyl groups; N-alkylaminosulphonylalkyl groups; N,N-dialkylaminosulphonylalkyl groups; alkylsulphinylalkyl groups; alkylsulphonyl groups; alkylcarbonyalkyl groups; aminoalkyl groups; and aminoalkyl groups in which said amine is substituted with at least one group chosen from alkyl groups, monohydroxyalkyl groups, polyhydroxyalkyl groups, alkylcarbonyl groups, formyl groups, trifluoroalkylcarbonyl groups, alkylcarboxyl groups, carbamyl groups; N-alkylcarbamyl groups, N,N-dialkylcarbamyl groups, thiocarbamyl groups, alkylsulphonyl groups, —Z groups, —COZ groups, and —COOZ groups;

Z, which may be identical or different, are each chosen from groups having formula (II) and groups having formula (III):

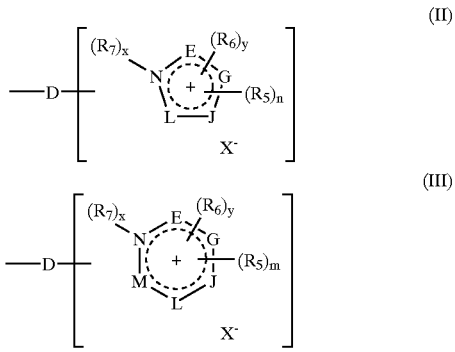

wherein

D, which may be identical or different, are each chosen from linear divalent alkyl chains and branched divalent alkyl chains, which chains may comprise from 1 to 14 carbon atoms, may be interrupted by at least one heteroatom, may be substituted with at least one group chosen from hydroxyl and $C_1$–$C_6$ alkoxy groups, and may comprise at least one ketone group;

E, G, J, L and M, which may be identical or different, are each chosen from carbon atoms; oxygen atoms; sulphur atoms; and nitrogen atoms;

n is an integer ranging from 0 to 4;

m is an integer ranging from 0 to 5;

$R_5$, which may be identical or different, are each chosen from a bond to D;—Z groups; halogens; hydroxyl groups; $C_1$–$C_6$ alkyl groups; $C_1$–$C_6$ monohydroxyalkyl groups; $C_2$–$C_6$ polyhydroxyalkyl groups; nitro groups; cyano groups; cyano ($C_1$–$C_6$)alkyl groups; $C_1$–$C_6$ alkoxy groups; tri($C_1$–$C_6$)alkylsilane($C_1$–$C_6$)alkyl groups; amido groups; aldehyde groups; carboxyl groups; ($C_1$–$C_6$)alkylcarbonyl groups; thio groups; $C_1$–$C_6$ thioalkyl groups; $C_1$–$C_6$ alkylthio groups; amino groups; amino groups protected with at least one group chosen from ($C_1$–$C_6$)alkylcarbonyl groups, carbamyl groups, and $C_1$–$C_6$ alkylsulphonyl groups; and groups chosen from NHR" groups and NR"R'" groups in which R" and R'", which may be identical or different, are each chosen from $C_1$–$C_6$ alkyl groups, $C_1$–$C_6$ monohydroxyalkyl groups, and $C_2$–$C_6$polyhydroxyalkyl groups;

$R_6$ is chosen from a bond to D; $C_1$–$C_6$ alkyl groups; $C_1$–$C_6$ monohydroxyalkyl groups; $C_2$–$C_8$ polyhydroxyalkyl groups; cyano($C_1$–$C_6$)alkyl groups; tri($C_1$–$C_6$)alkylsilane($C_1$–$C_6$)-alkyl groups; ($C_1$–$C_6$) alkoxy($C_1$–$C_6$)alkyl groups; carbamyl($C_1$–$C_6$)alkyl groups; ($C_1$–$C_6$)-alkylcarboxy($C_1$–$C_6$)alkyl groups; benzyl groups; and Z groups;

$R_7$ is chosen from a bond to D; $C_1$–$C_6$ alkyl groups; $C_1$–$C_6$ monohydroxyalkyl groups; $C_2$–$C_6$ polyhydroxyalkyl groups; aryl groups; benzyl groups; $C_1$–$C_6$ aminoalkyl groups; $C_1$–$C_6$ aminoalkyl groups wherein said amine is protected with at least one group chosen from ($C_1$–$C_6$)alkylcarbonyl groups, carbamyl groups, and $C_1$–$C_6$ alkylsulphonyl groups; carboxy($C_1$–$C_6$) alkyl groups; cyano($C_1$–$C_6$)alkyl groups; carbamyl ($C_1$–$C_6$)alkyl groups; $C_1$–$C_6$ trifluoroalkyl groups; tri($C_1$–$C_6$)alkylsilane($C_1$–$C_6$)alkyl groups; $C_1$–$C_6$ sulphonamidoalkyl groups; ($C_1$–$C_6$)alkylcarboxy($C_1$–$C_6$)alkyl groups; ($C_1$–$C_6$)alkylsulphinyl($C_1$–$C_6$) alkyl groups; ($C_1$–$C_6$)alkylsulphonyl($C_1$–$C_6$)alkyl groups; ($C_1C_6$)alkylketo($C_1$–$C_6$)alkyl groups; N—($C_1$–$C_6$)alkylcarbamyl($C_1$–$C_6$)alkyl groups; and N—($C_1$–$C_6$)alkylsulphonamido($C_1$–$C_6$)alkyl groups;

x and y, which may be identical or different, are integers chosen from 0 and 1, with the proviso that, in said groups having formula (II):
when x=0, D is attached to the nitrogen atom of the ring;
when x=1, D is attached to at least one of E, G, J and L;
when y=1:
E, G, J and L each simultaneously represent a carbon atom, and $R_6$ is bonded to the nitrogen atom of the ring of formula (II); or
at least one of E, G, J and L is chosen from a nitrogen atom to which $R_6$ is bonded;
and with the proviso that, in said groups having formula (III):
when x=0, D is attached to the nitrogen atom of the ring;
when x=1, D is attached to at least one of E, G, J, L and M;
when y=1, at least one of E, G, J, L and M is chosen from divalent atoms and $R_6$ is bonded to the at least one nitrogen atom of the ring of formula (III);

$X^8$, which may be identical or different, are each chosen from monovalent anions and divalent anions;
and with the proviso that in said amine of formula (I), at least one of $R_1$, $R_2$, $R_3$, and $R_4$ comprises at least one Z group, and (b) at least one compound chosen from aldehydes; ketones; quinones; diimindoisoindoline derivatives; and 3-aminoisoindolone derivatives;
with the proviso that said composition does not comprise an oxidizing agent.

29. A composition according to claim 28, wherein said at least one keratin fiber is a human keratin fiber.

30. A composition according to claim 29, wherein said human keratin fiber is hair.

31. A composition according to claim 28, further comprising at least one medium suitable for dyeing.

32. A composition according to claim 28, wherein said at least one heteroatom is chosen from oxygen; sulphur; and nitrogen.

33. A composition according to claim 28, wherein said monovalent anions and divalent anions are chosen from halogens; hydroxide anions; hydrogen sulphate anions; and alkyl sulphate anions.

34. A composition according to claim 33, wherein said halogens are chosen from chlorine; bromine; fluorine; and iodine.

35. A composition according to claim 33, wherein said alkyl sulphate anions are chosen from methyl sulphate and ethyl sulphate.

36. A composition according to claim 28, wherein said at least one compound is chosen from aldehydes having formula (IV) and the cosmetically acceptable salts thereof:

(IV)

in which $R_8$ is chosen from groups having formula (IV A):

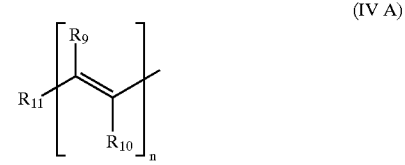

(IV A)

in which:

$R_9$ and $R_{10}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_9$ and $R_{10}$, which may be identical or different, may also form, together with the atoms to which they are attached, at least one ring, optionally substituted, chosen from aryl rings; 5-membered heterocyclic rings; and 6-membered heterocyclic rings;

n is an integer ranging from 0 to 3; and $R_{11}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted.

37. A composition according to claim 28, wherein said at least one compound is chosen from ketones having formula (V), ketones having formula (VI), and the cosmetically acceptable salts thereof:

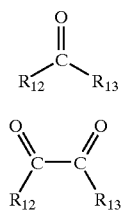
(V)

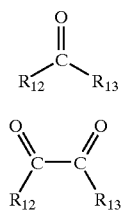
(VI)

in which:
- R$_{12}$ is chosen from hydrogen; alkyl groups; monohydroxyalkyl groups; polyhydroxyalkyl groups; alkylhydroxyalkyl groups; alkoxy groups; —CF$_3$ groups; and —OCF$_3$ groups;
- R$_{13}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and
- R$_{12}$ and R$_{13}$ may also form, together with the atoms to which they are attached, at least one ring chosen from 5-membered aryl rings; 6-membered aryl rings; and heterocyclic rings, it being possible for said at least one ring itself to be attached to at least one additional ring, optionally substituted, which may be identical or different from said at least one ring, wherein said at least one additional ring is chosen from 5-membered aryl rings; 6-membered aryl rings; and heterocyclic rings.

38. A composition according to claim 37, wherein said heterocyclic ring comprises at least one heteroatom chosen from N and S.

39. A composition according to claim 28, wherein said at least one compound is chosen from quinones having formula (VII), quinones having formula (VIII), and the cosmetically acceptable salts thereof:

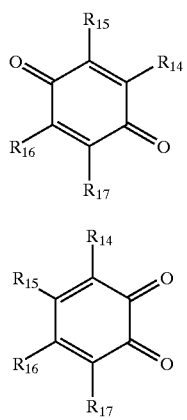
(VII)

(VIII)

in which:
- R$_{14}$ is chosen from hydrogen; halogens; sulphonic groups; and alkoxy groups;
- R$_{15}$, R$_{16}$ and R$_{17}$, which may be identical or different, are chosen from hydrogen, halogens; hydroxyl groups; alkyl groups; monohydroxyalkyl groups; polyhydroxyalkyl groups; alkylhydroxyalkyl groups; alkylsulphonyl groups; carboxyalkyl groups; aminoalkyl groups; alkylaminoalkyl groups; (dihydroxy)alkylaminoalkyl groups; alkyl-NR'R" groups wherein R' and R", which may be identical or different, are each chosen from alkyl groups, or R' and R" may also form, together with the nitrogen atom to which they are attached at least one ring chosen from aryl rings, 5-membered heterocycles, and 6-membered heterocycles; aryl groups; and amino groups, optionally substituted with at least one group chosen from alkyl groups and hydroxyalkyl groups; and
- at least one of R$_{14}$ and R$_{15}$, R$_{15}$ and R$_{16}$, and R$_{16}$ and R$_{17}$, may also form, together with the atoms to which they are attached, at least one ring, optionally substituted, chosen from aryl rings; 5-membered heterocycles; and 6-membered heterocycles.

40. A composition according to claim 28, wherein said at least one compound is chosen from diaminoisoindolines having formula (IX), 3-aminoisoindolone derivatives having formula (IX), and the cosmetically acceptable salts thereof:

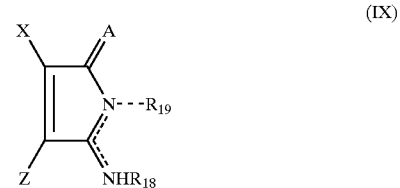
(IX)

in which:
- R$_{18}$ and R$_{19}$, which may be identical or different, are each chosen from hydrogen; alkyl groups; monohydroxyalkyl groups; polyhydroxyalkyl groups; alkylhydroxyalkyl groups; aminoalkyl groups; alkylaminoalkyl groups; (dihydroxy)alkylaminoalkyl groups; and alkyl-NR'R" groups wherein R' and R", which may be identical or different, are each chosen from alkyl groups, or may also form, together with the nitrogen atom to which they are attached, at least one ring chosen from aryl rings; 5-membered heterocycles; and 6-membered heterocycles;
- A is chosen from oxygen and NH; and
- X and Z form, together with the atoms to which they are attached, at least one ring, optionally substituted, chosen from aryl rings; 5-membered heterocycles; and 6-membered heterocycles.

41. A composition according to claim 28, having a pH ranging from 2 to 11.

42. A composition according to claim 28, wherein said at least one heterocyclic cationic amine is present in a concentration ranging from 0.1% to 10% by weight relative to the total weight of said composition.

43. A composition according to claim 42, wherein said at least one heterocyclic cationic amine is present in a concentration ranging from 0.5% to 5% by weight relative to the total weight of said composition.

44. A composition according to claim 28, wherein said at least one compound is present in a concentration ranging from 0.1% to 10% by weight relative to the total weight of the composition.

45. A composition according to claim 44, wherein said at least one compound is present in a concentration ranging from 0.5% to 5% of weight relative to the total weight of the composition.

46. A composition according to claim 31, wherein said at least one medium suitable for dyeing is an aqueous medium chosen from water and organic solvents.

47. A composition according to claim 46, wherein said organic solvents are chosen from alcohols; glycols ethers; and mixtures thereof.

48. A composition according to claim 31, wherein said at least one medium is present in a concentration ranging from 0.5% to 20% by weight relative to the total weight of said composition.

49. A composition according to claim 28, further comprising at least one fatty amide.

50. A composition according to claim 49, wherein said at least one fatty amide is chosen from monoethanolamides of acids derived from copra; monoethanolamides of lauric acid; monoethanolamides of oleic acid; diethanolamides of acids derived from copra; diethanolamides of lauric acid; and diethanolamides of oleic acid.

51. A composition according to claim 49, wherein said at least one fatty amide is present in a concentration ranging from 0.05% to 10% of weight relative to the total weight of said composition.

52. A composition according to claim 28, further comprising at least one surfactant.

53. A composition according to claim 52, wherein said at least one surfactant is chosen from anionic surfactants; cationic surfactants; nonionic surfactants; amphoteric surfactants; and zwitterionic surfactants.

54. A composition according to claim 52, wherein said at least one surfactant is present in a concentration ranging from about 0.1% to about 50% by weight relative to the total weight of said composition.

55. A composition according to claim 54, wherein said at least one surfactant is present in a concentration ranging from about 1% to about 20% by weight relative to the total weight of said composition.

56. A composition according to claim 28, further comprising at least one thickener.

57. A composition according to claim 56, wherein said at least one thickener is present in a concentration ranging from about 0.2% to about 20% by weight relative to the total weight of said composition.

58. A composition according to claim 28, further comprising at least one cosmetically acceptable adjuvant chosen from antioxidants; fragrances; sequestering agents; dispersants; hair conditioners; preserving agents; and opacifiers.

59. A composition according to claim 28, wherein said composition is in the form of a liquid, a cream or a gel.

60. A composition according to claim 28, wherein said groups having the formula (II) are chosen from pyrrole rings; imidazole rings; pyrazole rings; oxazole rings; thiazole rings; and triazole rings.

61. A composition according to claim 28, wherein said groups having the formula (III) are chosen from pyridine rings; pyrimidine rings; pyrazine rings; oxazine rings; and triazine rings.

62. A composition according to claim 28, wherein said at least one heterocyclic cationic amine is chosen from amines having formula (I), wherein said amines having formula (I) are chosen from:

1-[3-((2,4-diaminophenoxy)propyl]-3-methyl-3H-imidazol-1-ium chloride;

1-[(3-hydroxy-4-methylphenylcarbamoyl)methyl]-3-methyl-3H-imidazol-1-ium chloride;

3-ethyl-1-[(3-hydroxyphenylcarbamoyl)methyl]-3H-imidazol-1-ium chloride;

1-[(3-hydroxy-2,4-dimethylphenylcarbamoyl)methyl]-3-methyl-3H-imidazol-1-ium chloride;

1-[4-chloro-3-hydroxyphenylcarbamoyl)methyl]-3-ethyl-3H-imidazol-1-ium chloride;

1-[(3-hydroxy-4-methoxyphenylcarbamoyl)methyl]-3-methyl-3H-imidazol-1-ium chloride;

1-[(3-hydroxy-4-methoxyphenylcarbamoyl)methyl]-2-methyl-2H-pyrazol-1-ium chloride;

1-[2-(3-hydroxy-4-methylphenylamino)ethyl]-3-methyl-3H-imidazol-1-ium bromide;

1-[2-(3-hydroxy-4-methylphenylcarbamoyloxy)ethyl]-2,3-dimethyl-3H-imidazol-1-ium chloride;

1-{[3-amino-4-(3-(3-methyl-3H-imidazol-1-ium) propoxy)-phenylcarbamoyl]methyl}-3-methyl-3H-imidazol-1-ium dichloride;

3-(3-trimethylammonium-2-hydroxypropyl)-1-[(3-hydroxy-4-methylphenylcarbamoyl)methyl]-3H-imidazol-1-ium dichloride;

1-{[2-(2,4-diaminophenoxy)ethylcarbamoyl]methyl}-3-methyl-3H-imidazol-1-ium chloride;

1-[(2,4-dihydroxyphenylcarbamoyl)methyl]-3-methyl-3H-imidazol-1-ium chloride;

N,N-bis[2-(3-methyl-3H-imidazol-1-ium) ethyl]benzene-1,3-diamine dichloride;

1-{3-[4-amino-2-(2-triethylammoniumacetylamino) phenoxy]propyl}-3-methyl-3H-imidazol-1-ium dichloride;

1-(3-{4-amino-2-[2-(3-methyl-3H-imidazol-1-ium)-acetylamino]phenoxy}propyl)-1,4-dimethylpiperazin-1-ium dichloride;

1-[2-(2,4-dihydroxyphenyl)-2-oxoethyl]-3-methyl-3H-imidazol-1-ium chloride;

1-[2-(2,4-diaminophenyl)ethyl]-3-methyl-3H-imidazol-1-ium chloride;

1-bis-1-{3-[3-(2,4-diaminophenoxy)propyl]-3H-imidazol-1-ium}butane dichloride monohydrate;

1,3-bis[3-(2,4-diaminophenoxy)propyl]-3H-imidazol-1-ium chloride;

3-[3-(2,4-diaminophenoxy)propyl]-1-[(3-hydroxy-4-methylphenylcarbamoyl)methyl]-3H-imidazol-1-ium chloride;

1,4-bis{3-[(3-hydroxy-4-methylphenylcarbamoyl) methyl]-3H-imidazol-1-ium}butane dichloride;

1,4-bis-{3-[2-(2,4-diaminophenyl)ethyl]-3H-imidazol-1-ium}butane dichloride;

1,4-bis-{3-[2-(3-hydroxy-4-methylphenylamino)ethyl]-3H-imidazol-1-ium}butane dibromide;

1,4-bis{3-[(2,4-dihydroxyphenylcarbamoyl)methyl]-3H-imidazol-1-ium}butane dichloride;

3-[3-(2,4-diaminophenoxy)propyl]-1-[(2,4-dihydroxyphenylcarbamoyl)methyl]-3H-imidazol-1-ium chloride;

3-[3-(2-aminophenylamino)propyl]-1-methyl-3H-imidazol-1-ium monochloride;

3-[2-(2-aminophenylamino)ethyl]-1-methyl-3H-imidazol-1-ium monochloride;

4-[2-(1-methyl-3H-imidazol-1-ium)ethoxy-N2-[2-(1-methyl-3H-imidazol-1-ium)ethyl]benzene-1,2-diamine dichloride;

3-[2-(2-amino-4-methylphenylamino)ethyl]-1-ethyl-3H-imidazol-1-ium monochloride;

3-[3-(2-aminophenylamino)propyl]-1-(3-trimethylammonium-2-hydroxypropyl)-3H-imidazol-1-ium dichloride;

3-[3-(2-aminophenylamino)propyl]-1-(2-hydroxyethyl)-3H-imidazol-1-ium monobromide;

3{[2-(2-aminophenylamino)ethylcarbamoyl]methyl}-1-methyl-3H-imidazol-1-ium monochloride;

1-[2-(2-amino-4-chlorophenylamino)ethyl]pyridinium monochloride;

3-[2-(2-amino-5-methoxyphenylamino)ethyl]-1-methyl-3H-imidazol-1-ium monochloride;

3-[2-(2-amino-5-methylsulphanylphenylamino)ethyl]-1-methyl-3H-imidazol-1-ium monochloride;

1-[2-(4-aminophenylamino)ethyl]-3-methyl-3H-imidazol-1-ium bromide;

1-[3-(2,5-diaminophenoxy)propyl]-3-methyl-3H-imidazol-1-ium chloride;

3-[3-(4-aminophenylamino)propyl]-1-methyl-3H-imidazol-1-ium chloride;

3-[3-(4-amino-3-methylphenylamino)propyl]-1-methyl-3H-imidazol-1-ium chloride;

3-[3-(4-amino-2-methylphenylamino)propyl]-1-methyl-3H-imidazol-1-ium chloride;

3-[3-(4-amino-2-fluorophenylamino)propyl]-1-methyl-3H-imidazol-1-ium chloride monohydrate;

3-[3-(4-amino-2-cyanophenylamino)propyl]-1-methyl-3H-imidazol-1-ium chloride;

1-[2-(4-amino-2-methoxyphenylamino)ethyl]-3-methyl-3H-imidazol-1-ium choride;

and the acid addition salts thereof.

63. A composition according to claim 28, wherein said at least one heterocyclic cationic amine is chosen from amines having formula (I), wherein said amines having formula (I) are chosen from:

1-(5-amino-2-hydroxybenzyl)-3-methyl-3H-imidazol-1-ium chloride;

1-(5-amino-2-hydroxybenzyl)-2-methyl-2H-pyrazol-1-ium chloride;

1-[2-(2,5-diaminophenyl)ethyl]-3-methyl-3H-imidazol-1-ium chloride;

1,3-bis-1-{3-{3'-[(4"-amino-3"-methylanilino)-N-propyl]}-3H-imidazol-1-ium}propane dichloride;

1,3-bis-1-{3-{3'-[(4"-amino-2"-methylanilino)-N-propyl]}-3H-imidazol-1-ium}propane dichloride monohydrate diethanol;

1,3-bis-1-{3-{3"-aminoanilino)-N-propyl]}-3H-imidazol-1-ium}propane dichloride monohydrate ethanol;

1,3-bis-1-{3-{3'-[(4"amino-2"-methylanilino)-N-propyl]}-3H-imidazol-1-ium}-2-propanol dichloride monohydrate;

1,4-bis-1-{3-[3-(2,5-diaminophenoxy)propyl]-3H-imidazol-1-ium}butane dichloride dihydrate;

1,3-bis[3-(2,5-diaminophenoxy)propyl]-3H-imidazol-1-ium monochloride monohydrate;

1,4-bis-1-(5-amino-2-hydroxybenzyl)-3H-imidazol-1-ium]butane dichloride monohydrate;

1,3-bis{3-{3-[(2-aminoanilino)-N-propyl]}-3H-imidazol-1-ium}propane dibromide;

1,4-bis{3-{2-[(2-aminoanilino)-N-ethyl]}-3H-imidazol-1-ium}butane dichloride;

1-[2-(2-aminoanilino)ethyl]-3-[3-(2-aminoanilino)propyl]-3H-imidazol-1-ium monochloride;

and the acid addition salts thereof.

64. A composition according to claim 28, wherein said at least one compound is chosen from benzaldehyde;
2-monohydroxybenzaldehyde;
3-monohydroxybenzaldehyde;
4-monohydroxybenzaldehyde;
2-monomethoxybenzaldehyde;
3-monomethoxybenzaldehyde;
4-monomethoxybenzaldehyde;
2-monomethoxybenzaldehyde;
3-monomethylbenzaldehyde; 4-monomethylbenzaldehyde;
(2,3)-dihydroxybenzaldehyde; (2,4)-dihydroxybenzaldehyde; (2,5)-dihydroxy benzaldehyde;
(2,6)-dihydroxybenzaldehyde; (3,5)-dihydroxybenzaldehyde; (2,3)-dimethoxybenzaldehyde;
(2,4)-dimethoxybenzaldehyde; (2,5)-dimethoxybenzaldehyde; (2,6)-dimethoxybenzaldehyde;
(3,5)-dimethoxybenzaldehyde; vanillin; isovanillin; syringaldehyde; orthophthalaldehyde; isophthalaldehyde; terephthalaldehyde; (2,3)-dimethyl benzaldehyde; (2,4)-dimethylbenzaldehyde; (2,5)-dimethylbenzaldehyde, (2,6)-dimethylbenzaldehyde; (3,5)-dimethylbenzaldehyde;
4-isopropylbenzaldehyde; 4-dimethylaminobenzaldehyde;
4-diethylaminobenz aldehyde; piperonal; (2,6)-dimethyl-4-hydroxybenzaldehyde; (3,5-dimethyl-4-hydroxybenzaldehyde; 2-mononitrobenzaldehyde;
3-mononitrobenzaldehyde; 4-mononitrobenzaldehyde;
2-hydroxy-3-methoxybenzaldehyde; 2-hydroxy-4-methoxybenzaldehyde; 2-hydroxy-5-methoxybenzaldehyde; 2-hydroxy-6-methoxybenzaldehyde; 4-methylthiobenzaldehyde; (2,3,4)-trihydroxybenzaldehyde; (2,4,6)-trihydroxybenzaldehyde;
(3,4,5)-tri hydroxybenzaldehyde; (2,4,5)-trihydroxybenzaldehyde; methyl 2-formyl benzoate; methyl 3-formyl benzoate; methyl 4-formyl benzoate; 2-mono(2-hydroxyethoxy)benzaldehyde; 3-mono(2-hydroxyethyl)benzaldehyde; 4-mono(2-hydroxyethyl)benzaldehyde;
4-nitro-3-hydroxybenzaldehyde; 3-nitro-4-hydroxybenzaldehyde; 2-nitro-4-hydroxyaldehyde; 3-nitro-2-hydroxybenzaldehyde; 2-monotrifluorobenzaldehyde; 3monotrifluorobenzaldehyde;
4-monotrifluorobenzaldehyde; 2,3-dihydroxy-4-methoxybenzaldehyde; 3,4-dihydroxy-5-methoxybenzaldehyde; 3,5-dihydroxy-4-methoxybenzaldehyde; 3-methoxy-2-nitrobenzaldehyde;
4-methoxy-3-nitro benzaldehyde; (2,3,4-trimethoxybenzaldyde; (2,4,6)-trimethoxybenzaldehyde;
(3,4,5)-trimethoxybenzaldehyde; (2,4,5)-trimethoxybenzaldehyde; 5-nitrovanillin; (2,4)-dinitrobenzaldehyde; (2,6)dinitrobenzaldehyde; pentamethylbenzaldehyde; 4-methylsulphonylbenzaldehyde;
2-monoformylphenoxyacetic acid; 3-monoformylphenoxyacetic acid; 4-monoformylphenoxyacetic acid; 4-diethylaminosalicylaldehyde; 4-(3-dimethylaminopropoxy) benzaldehyde; 2,3-dihydrobenzo(b)furan-5-carboxaldehyde; 1-naphthaldehyde; 2-naphthaldehyde;
6-carboxaldehyde-1,4-benzodioxane; 5-carboxaldehyde-1,4-benzodioxane; 2-monohydroxy-1-naphthaldehyde;
4-monohydroxy-1-naphthaldehyde; 1-mono-hydroxy-2-naphthaldehyde; 1-(4-formylphenyl)imidazole;
4-pyrrolidino-benzaldehyde; 2-monomethoxy-1-naphthaldehyde; 4-monomethoxy-1-naphthaldehyde; 2,3-dimethylchroman-6-carboxyaldehyde; 2,3,6,7-tetrahydro-1H,5H-pyrido(3,2,1-lJ)quinoline-9-carbaldehyde;
4-dimethylamino-1-naphthaldehyde; 9-anthraldehyde;
3-nitro-4-pyrrolidinobenzaldehyde; 3-nitro-4-piperidinobenzaldehyde; 3-nitro-4-morpholinobenzaldehyde;
pyridine-2-monocarboxaldehyde; pyridine-3-monocarboxaldhyde; pyridine-4-monocarboxaldehyde; 2,6-pyridinodicarboxaldehyde; 5-formyl-6-methyluracil; pyridoxal; quinoline-2-monocarboxaldehyde; quinoline-3-monocarboxaldehyde; quinoline-4-monocarboxaldehyde;
8-hydroxyquinoline-2-carboxaldehyde; 2-furaldehyde;

3-furaldehyde; 2-thienylcarboxaldehyde; 3-thienylcarboxaldehyde; 2-imidazocarboxaldehyde; 3-imidazocarboxaldehyde; 2-pyrrolecarboxaldehyde; 5-nitro-2-furaldehyde; 5-(dimethylamino)-2-furaldehyde; 2,5-thiophenedicarboxaldehyde; 2,3-thiophenedicarboxaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4-monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

65. A composition according to claim 28, wherein said at least one compound is chosen from 2,3-indolinedione; 2,3-butanedione; 2,3-pentanedione; (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis (dimethylamino)benzil; camphoroquinone; cyclohexane-1, 2-dione; isatin; N-methylisatin; 4-monomethylisatin; 5-monomethylisatin; 6-monomethylisatin; 7-monomethylisatin; (4,5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5sulphonic acid; 2,4,5-trihydroxypyrimidine; alloxan; 1,3-dimethylhexahydro-2,4, 5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxyoxindole; 5-monochlorooxindole; and 6-monochlorooxindole.

66. A composition according to claim 28, wherein said at least one compound is chosen from 1,4-naphthoquinone; spinulosin; atromentin; aurentiogliocladin; 2,5-dihydroxy-6-methylbenzoquinone; 2-hydroxy-3-methyl-6-methoxybenzoquinone; 2,5-dihydroxy-3,6-diphenylbenzoquinone; 2,3-dimethyl-5-hydroxy-6-methoxybenzoquinone; 2,5-dihydroxy-6-isopropylbenzoquinone; lawsone; juglone; fafioline; naphthazarine; naphthopurpurine; lapachol; plumbagin; chloroplumbagin; droserone; shikonine; 2-hydroxy-3-methyl-1,4-naphthoquinone; 3,5-dihydroxy-1,4-naphthoquinone; 2,5-dihydroxy-1,4-naphthoquinone; 2-methoxy-5-hydroxy-1,4-naphthoquinone; 3-methoxy-5hydroxy-1,4-naphthoquinone; (1,4)-naphthoquinone; (1,2)-naphthoquinone; 4,5-dimethoxy-1,2-benzoquinone; phenanthrenequinone; and (1,2)-naphtho quinone-4-sulphonic acid.

67. A composition according to claim 28, wherein said at least one compound is chosen from 3-imino-3H-isoindolylamine; 3-imino-4-methyl-3H-isoindol-1-ylamine; 3-imino-4-tert-butyl-3H-isoindol-1-ylamine; 3-imino-7-nitro-3H-isoindol-1-ylamine; 3-amino-1-imino-1H-isoindol-4-ol; 3-imino-7-isopropoxy-3H-isoindol-1-ylamine; 3-imino-7-(2,2,2-trifluoroethoxy)-3H-isoindol-1-ylamine; 3-imino-7-ethoxy-3H-isoindol-1-ylamine; 3-imino-7-butoxy-3H-isoindol-1-ylamine; 3-amino-1-imino-1H-isoindole-4-sulphonic acid; 3-imino-7-chloro-3H-isoindol-1-ylamine; 3-imino-5-methyl-3H-isoindol-1-ylamine; 3-imino-5-ethyl-3H-isoindol-1-ylamine; 3-imino-5-tert-butyl-3H-isoindol-1-ylamine; 3imino-5-amino-3H-isoindol-1-ylamine; N-(1-amino-3-imino-3H-isoindol-5-yl) acetamide; 3-imino-5-nitro-3H-isoindol-1-ylamine; 3imino-5-fluoro-3H-isoindol-1-ylamine; 3imino-5-chloro-3H-isoindol-1-ylamine; 3-imino-5-methylsulphanyl-3H-isoindol-1-ylamine; 3-imino-5-methoxy-3H-isoindol-1-ylamine; 3imino-5-ethoxy-3H-isoindol-1ylamine; 3-imino-5-propoxy-3H-isoindol-1-ylamine; 3-imino-5-isopropoxy-3H-isoindol-1-yl amine; 3-imino-5butoxy-3H-isoindol-1ylamine; 3-imino-5-isobutoxy-3H-isoindol-1-ylamine; 3-imino-5tert-butoxy-3H-isoindol-1-ylamine; 3imino-5-(2, 2,2-trifluoro methyl)-3H-isoindol-1-ylamine; 3-imino-5-(2, 2,2-trifluoroethoxy)-3H-isoindol-1-ylamine; 3-imino-5-methane sulphonyl-3H-isoindol-1-ylamine; 3-imino-5,6-dimethyl-3H-isoindol-1-ylamine; 3-imino-5,6-diethyl-3H-isoindol-1-ylamine; 3-imino-5,6-dimethoxy-3H-isoindol-1-ylamine; 3imino-5,6-diethoxy-3H-isoindol-1-ylamine; 3-imino-5,6-dibutoxy-3H-isoindol-1-ylamine; 3-imino-5,6-bis(trifluoromethyl)3H-isoindol-1-ylamine; 3-imino-5,6-dichloro-3H-isoindol-1-ylamine; 5,6-bis(ethoxymethyl)3-imino-3H-isoindol-1-ylamine; 3-amino-1-imino-1H-isoindole-4,7-diol; 4,7-dichloro-3-imino-3H-isoindol-1-ylamine; 4,5,7-trichloro-3-imino-N6,N6-dimethyl-3H-isoindole-1,6-diamine; 4,5,6,7-tetrachloro-3-imino-3H-isoindol-1-ylamine; 4,5,6,7-tetrafluoro-3-imino-3H-isoindole-1-ylamine; 3-butylimino-3H-isoindol-1-ylamine; 2-(3-aminoisoindol-1-ylideneamino)ethanol; 3-(3-aminoisoindol-1-ylideneamino)-3-methylpentane-1,5-diol; N-(3-aminoisoindol-1-ylidene)guanidine; 7-imino-7H-pyrrolo[3,4-b]pyrid-5-ylamine; 7-imino-7H-pyrrolo[3,4-b]pyrazin-5-ylamine; 7-imino-2,3-dimethyl-7H-pyrrolo[3,4-b]pyrazin-5ylamine; 7-imino-7H-[1,4]-dithiino[2,3-c]pyrrol-5-ylamine; 7-imino-2,3-dimethyl-7H-[1,4]dithiino[2, 3-c]pyrrol-5ylamine; 7-imino-2,3-dihydro-7H-[1,4]dithiino [2,3-c]pyrrol-5-ylamine; 3-aminoisoindol-1-one; 3-amino-7-hydroxymethyl isoindol-1-one; 3-amino-7-methylisoindol-1-one; 3-amino-7-chloroisoindol-1-one; 3-amino-4-chloroisoindol-1-one; 3-amino-1-oxo-1H-isoindole-4-sulphonic acid; 3-amino-4-nitroisoindol-1-one; 3amino-6-nitroisoindol-1-one; 3-amino-6-methyl-isoindol-1-one; 3-amino-6-methyl sulphanylisoindol-1-one; 3-amino-6-methoxyisoindol-1-one; 3-amino-5-chloroisoindol-1-one; 3-amino-5-fluoro-isoindol-1-one; 3-amino-5-methoxyisoindol-1-one; 3-amino-5-nitroisoindol-1-one; ethyl 3-amino-1oxo-1H-isoindole-5-carboxylate 3-amino-5, 6-dichloroisoindol-1-one; 3-amino-5,6-dibromoisoindol-1-one; 3-amino-4,7-dichloroisoindol-1-one; 3-amino-4,5,7-trichloroisoindol-1-one; 3-amino-4,5,6, 7tetrachloroisoindol-1-one; 3-amino-4,5,7-trichloro-6-methylsulphanylisoindol-1-one; 3-amino-4,5,6,7-tetra-bromoisoindol-1-one; 3-amino-4,5,6,7-tetrafluoroisoindol-1-one; 3-methylamino-isoindol-1-one; 3-ethylaminoisoindol-1-one; 3-propylaminoisoindol-1-one; 3-dimethylaminoisoindol-1-one; 7-ethylaminopyrrolo[3,4-b]pyrid-5-one; 7-aminopyrrolo[3,4-b]pyrid-5-one; 3-aminopyrrolo[3,4-c]pyrid-5-one; 3-amino-6-methylpyrrolo[3,4-c]pyrid-1-one; 5-aminopyrrolo[3,4-b]pyrid-7-one; 7-aminopyrrolo[3,4-b]pyrazin-5-one; 7-amino-2-methylpyrrolo[3,4-b]pyrazin-5-one; 7-amino-2,3-dimethylpyrrolo[3,4-b]pyrazin-5-one; 7-amino-2,3-dihydro-[1,4]dithiino[2,3-c]pyrrol-5-one; 3-imino-2-methyl-2,3-dihydroisoindol-1-one; 3-imino-2-ethyl-2,3- dihydroisoindol-1-one; 3-imino-2-propyl-2,3-dihydroisoindol-1-one; 2-hydroxymethyl-3-imino-2,3-dihydroisoindol-1-one; 2-(2-hydroxyethyl)-3-imino-2,3-dihydroisoindol-1-one; 2-(1-imino-3-oxo-1,3-dihydroisoindol-2-yl)ethanesulphonic acid; 3-(1-imino-3-oxo-1,3-dihydroisoindol-2-yl)propionic acid; 2-(3hydroxypropyl)-3-imino-2,3-dihydroisoindol-1-one and 5-imino-6-methyl-5,6-dihydropyrrolo[3,4-b]pyridin-7-one.

68. A composition according to claim 36, wherein said salts are chosen from hydrochlorides; sulphates; hydrobromides; and tartrates.

69. A composition according to claim 37, wherein said salts are chosen from hydrochlorides; sulphates; hydrobromides; and tartrates.

70. A composition according to claim 39, wherein said salts are chosen from hydrochlorides; sulphates; hydrobromides; and tartrates.

71. A composition according to claim 40, wherein said salts are chosen from hydrochlorides; sulphates; hydrobromides; and tartrates.

72. A composition according to claim 62, wherein said salts are chosen from hydrochlorides; sulphates; hydrobromides; and tartrates.

73. A composition according to claim 63, wherein said salts are chosen from hydrochlorides, sulphates, hydrobromides and tartrates.

74. A composition according to claim 28, wherein said at least one compound is chosen from 1,4-dimethylaminobenzaldehyde and 4-dimethylaminonaphthaldehyde.

75. A multi-compartment device or dyeing kit, wherein said device or dyeing kit comprises at least two compartments, wherein:

(a) a first compartment comprises a component (A); and
(b) a second compartment comprises a component (B);

wherein said component (A) comprises at least one heterocyclic cationic amine; and wherein said component (B) comprises at least one compound chosen from aldehydes; ketones; quinones; diiminoisoindoline derivatives; and 3-aminoisoindolone derivatives;

and further wherein said device or dyeing kit does not comprise an oxidizing agent, and further wherein said at least one heterocyclic cationic amine is chosen from amines having formula (I) and the cosmetically acceptable salts thereof:

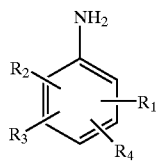

(I)

wherein:
$R_1$, $R_2$, $R_3$ and $R_4$, which may be identical or different, are each chosen from hydrogen; halogens; —$NH_2$ groups; —OH groups; —Z groups; —COZ groups; —COOZ groups; alkylcarbonyl groups; aminoalkylcarbonyl groups; NB alkylaminoalkylcarbonyl groups; N,N-dialkylaminoalkylcarbonyl groups; aminoalkylcarbonyl groups; N-alkylaminoalkylcarbonylalkyl groups; N,N-dialkylaminoalkylcarbonylalkyl groups; carboxyl groups; alkylcarboxyl groups; alkylsulphonyl groups; aminosulphonyl groups; N-alkylaminosulphonyl groups; N,N-dialkylaminosulphonyl groups; aminosulphonylalkyl groups; N-alkylaminosulphonylalkyl groups; N,N-dialkylaminosulphonylalkyl groups; carbamyl groups; N-alkylcarbamyl groups; N,N-dialkylcarbamyl groups; carbamylalkyl groups; N-alkylcarbamylalkyl groups; N,N-dialkylcarbamylalkyl groups; alkyl groups; monohydroxyalkyl groups; polyhydroxyalkyl groups; alkoxyalkyl groups; trifluoroalkyl groups; cyano groups; —$OR_l$ groups; —$SR_l$ groups; —$OR_lZ$ groups; —$SR_lZ$ groups; and amino groups protected with at least one group chosen from alkylcarboxyl groups, trifluoroalkylcarbonyl groups, aminoalkylcarbonyl groups, carbonyl groups, N-alkylaminoalkylcarbonyl groups, N,N-dialkylaminoalkylcarbonyl groups, alkylcarboxyl groups, carbamyl groups, N-alkylcarbamyl groups, N,N-dialkylcarbamyl groups, alkylsulphonyl groups, aminosulphonyl groups, N-alkylaminosulphonyl groups, N,N-dialkylamino sulphonyl groups, thiocarbamyl groups, formyl groups, —COZ groups, and —COOZ groups;

wherein
$R_1$, which may be identical or different, are each chosen from alkyl groups, monohydroxyalkyl groups; polyhydroxyalkyl groups; —Z groups; alkoxyalkyl groups; aryl groups; benzyl groups; carboxyalkyl groups; alkylcarboxyalkyl groups; cyanoalkyl groups; carbamylalkyl groups; N-alkylcarbamylalkyl groups; N,N-dialkylcarbamylalkyl groups; tri-fluoroalkyl fluoroalkyl groups; aminosulphonylalkyl groups; N-alkylaminosulphonylalkyl groups; N,N-dialkylaminosulphonylalkyl groups; alkylsulphinylalkyl groups; alkylsulphonylalkyl groups; alkylcarbonylalkyl groups; aminoalkyl groups; and aminoalkyl groups in which said amine is substituted with at least one group chosen from alkyl groups, monohydroxyalkyl groups, polyhydroxyalkyl groups, alkylcarbonyl groups, formyl groups, trifluoroalkylcarbonyl groups, alkylcarboxyl groups, carbamyl groups, N-alkylcarbamyl groups, N,N-dialkylcarbamyl groups, thiocarbamyl groups, alkylsulphonyl groups, —Z groups, —COZ groups, and —COOZ groups;

Z, which may be identical or different, are each chosen from groups having formula (II) and groups having formula (III):

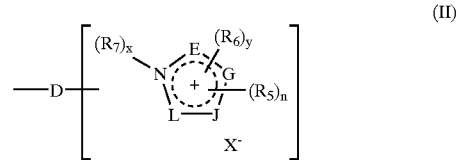

(II)

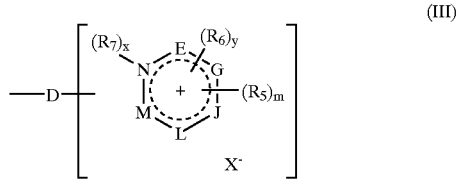

(III)

wherein
D, which may be identical or different, are each chosen from linear divalent alkyl chains and branched divalent alkyl chains, which chains may comprise from 1 to 14 carbon atoms, may be interrupted by at least one heteroatom, may be substituted with at least one group chosen from hydroxyl and $C_1$–$C_6$ alkoxy groups, and may comprise at least one ketone group;

E, G, J, L and M, which may be identical or different, are each chosen from carbon atoms; oxygen atoms; sulphur atoms; and nitrogen atoms;

n is an integer ranging from 0 to 4;

m is an integer ranging from 0 to 5;

$R_5$, which may be identical or different, are each chosen from a bond to D;—Z groups; halogens; hydroxyl groups; $C_1$–$C_6$ alkyl groups; $C_1$–$C_6$ monohydroxyalkyl groups; $C_2$–$C_6$ polyhydroxyalkyl groups; nitro groups; cyano groups; cyano($C_1$–$C_6$)alkyl groups; $C_1$–$C_6$ alkoxy groups; tri($C_1$–$C_6$)alkylsilane($C_1$–$C_6$)alkyl groups; amido groups; aldehyde groups; carboxyl groups; ($C_1$–$C_6$)alkylcarbonyl groups; thio groups; $C_1$–$C_6$ thioalkyl groups; $C_1$–$C_6$ alkylthio groups; amino groups; amino groups protected with at least one group chosen from ($C_1$–$C_6$)alkylcarbonyl groups, carbamyl groups, and $C_1$–$C_6$ alkylsulphonyl groups; and groups chosen from NHR" groups and NR"R'" groups in which R" and R'", which may be identical or different, are each chosen from $C_1$–$C_6$ alkyl groups, $C_1$–$C_6$ monohydroxyalkyl groups, and $C_2$–$C_6$ polyhydroxyalkyl groups;

$R_6$ is chosen from a bond to D; $C_1$–$C_6$ alkyl groups; $C_1$–$C_6$ monohydroxyalkyl groups; $C_2$–$C_6$ polyhydroxyalkyl groups; cyano($C_1$–$C_6$)alkyl groups; tri($C_1$–$C_6$)alkylsilane($C_1$–$C_6$)-alkyl groups; ($C_1$–$C_6$) alkoxy($C_1$–$C_6$)alkyl groups; carbamyl($C_1$–$C_6$)alkyl groups; ($C_1$–$C_6$)-alkylcarboxy($C_1$–$C_6$)alkyl groups; benzyl groups; and Z groups;

$R_7$ is chosen from a bond to D; $C_1$–$C_6$ alkyl groups; $C_1$–$C_6$ monohydroxyalkyl groups; $C_2$–$C_6$ polyhydroxyalkyl groups; aryl groups; benzyl groups; $C_1$–$C_6$ aminoalkyl groups; $C_1$–$C_6$ aminoalkyl groups wherein said amine is protected with at least one group chosen from ($C_1$–$C_6$)alkylcarbonyl groups, carbamyl groups, and $C_1$–$C_6$ alkylsulphonyl groups; carboxy($C_1$–$C_6$) alkyl groups; cyano($C_1$–$C_6$)alkyl groups; carbamyl ($C_1$–$C_6$)alkyl groups; $C_1$–$C_6$ trifluoroalkyl groups; tri($C_1$–$C_6$)alkylsilane($C_1$–$C_6$)alkyl groups; $C_1$–$C_6$ sulphonamidoalkyl groups; ($C_1$–$C_6$)alkylcarboxy($C_1$–$C_6$)alkyl groups; ($C_1$–$C_6$)alkylsulphinyl($C_1$–$C_6$)alkyl groups; ($C_1$–$C_6$)alkylsulphonyl($C_1$–$C_6$)alkyl groups; ($C_1$–$C_6$)alkylketo($C_1$–$C_6$)alkyl groups; N—($C_1$–$C_6$)alkylcarbamyl($C_1$–$C_6$)alkyl groups; and N—($C_1$–$C_6$)alkylsulphonamido($C_1$–$C_6$alkyl groups;

x and y, which may be identical or different, are integers chosen from 0 and 1, with the proviso that, in said groups having formula (II);

when x=0, D is attached to the nitrogen atom of the ring;

when x=1, D is attached at least one of E, G, J and L;

when y=1:

E, G, J and L each simultaneously represent a carbon atom, and $R_6$ is bonded to the nitrogen atom of the ring of formula (III); or at least one of E, G, J and L is chosen from a nitrogen atom to which $R_6$ is bonded;

and with the proviso that, in said groups having formula (III):

when x=0, D is attached to the nitrogen atom of the ring;

when x=1, D is attached to at least one of E, G, J, L and M;

when y=1, at least one of E, G, J, L and M is chosen from divalent atoms and $R_6$ is bonded to the at least one nitrogen atom of the ring of formula (III);

$X^8$, which may be identical or different, are each chosen from monovalent anions and divalent anions;

and with the proviso that in said amine of formula (I), at least one of $R_1$, $R_2$, $R_3$, and $R_4$ comprises at least one Z group.

76. A multi-compartment device or dyeing kit according to claim 75, wherein at least one component chosen from said component (A) and said component (B) is in the form of an anhydrous composition; and wherein said device or dyeing kit comprises a third compartment comprising a cosmetically acceptable aqueous medium which is suitable for dyeing and which is intended to be mixed, before use, into at least one compartment chosen from said first compartment comprising a component (A) and said second compartment comprising a component (B).

\* \* \* \* \*

UNITED STATES PATENT AND TRADEMARK OFFICE
CERTIFICATE OF CORRECTION

PATENT NO. : 6,451,067 B1
DATED : September 17, 2002
INVENTOR(S) : Alain Lagrange et al.

It is certified that error appears in the above-identified patent and that said Letters Patent is hereby corrected as shown below:

Column 18,
Line 45, after "wherein" insert a colon.
Line 46, after "are" insert -- each --.
Line 61, "N-alkylcarbamyalkyl group" should read -- N-alkylcarbamylalkyl groups --.
Line 65, "-$OR_1$ groups" should read -- -$OR_i$ groups --.
Line 66, "-$SR_1Z$ groups" should read -- -$SR_iZ$ groups --.

Column 19,
Line 11, "$R_1$" should read -- $R_i$ --.
Line 21, "arkylsulphonylalkyl" should read -- alkylsulphonylalkyl --.
Line 50, after "wherein" insert a colon.
Line 53, "1to 14" should read -- 1 to 14 --.

Column 20,
Line 1, before "$(C_1-C_6)$alkyl" delete the space.
Line 2, "groups," should read -- groups; --.
Line 5, before "alkylthio" insert a space.
Line 11, "$C_{1-C6}$" should read -- $C_1-C_6$ --.
Line 12, after "$C_2-C_6$" insert a space.
Line 17, "$(C_1-C_6)$alkylsilane-$(C_1-C_6)$alkyl" should read -- $(C_1-C_6)$alkylsilane$(C_1-C_6)$alkyl --.

Column 21,
Lines 3 and 6, "claim 2" should read -- claim 1 --.
Line 53, "substituted," should read -- substituted; --.

Column 24,
Line 21, "3methyl" should read -- 3-methyl --.
Line 37, "1,4-bis-" should read -- 1,4-bis --.
Lines 39 and 41, "1,4-bis" should read -- 1,4-bis- --.
Line 45, "propyl]1-[(2,4-" should read -- propyl]-1-[(2,4- --.
Line 54, "1methyl" should read -- 1-methyl --.

Column 25,
Line 32, "1[2-(2,5-diaminophenyl)" should read -- 1-[2-(2,5-diaminophenyl) --.
Line 55, "[2-aminoanilino)-N-ethyl]" should read -- [(2-aminoanilino)-N-ethyl] --.
Line 59, after "and" insert -- the --.

UNITED STATES PATENT AND TRADEMARK OFFICE
CERTIFICATE OF CORRECTION

PATENT NO. : 6,451,067 B1
DATED : September 17, 2002
INVENTOR(S) : Alain Lagrange et al.

It is certified that error appears in the above-identified patent and that said Letters Patent is hereby corrected as shown below:

Column 26,
Line 2, "dihydroxybenzaldhyde" should read -- dihydroxybenzaldehyde --.
Line 4, "dihydroxybenazldehyde" should read -- dihydroxybenzaldehyde --.
Line 13, "(4-isopropylbenzaldehyde" should read -- 4-isopropylbenzaldehyde --.
Line 24, "tri-hydroxybenzaldehyde" should read -- trihydroxybenzaldehyde --.
Line 37, "(2,3,4-" should read -- (2,3,4)- --.
Line 39, "(2,4,5-" should read -- (2,4,5)- --.
Line 40, "trimethoxybanzaldehyde" should read -- trimethoxybenzaldehyde --.
Line 56, "(3,2,1-lJ)" should read -- (3,2,1-IJ) --.
Line 40, "(2,4)" should read -- (2,4)- --.
Line 60, "monocarboxaldhyde" should read -- monocarboxaldehyde --.

Column 27,
Line 16, "(2,3-hexanedione" should read -- (2,3)-hexanedione --.
Line 16, "(3,4-" should read -- (3,4)- --.
Line 20, "4-mono-methylsatin" should read -- 4-mono-methylisatin --.
Line 22, "(4,7)" should read -- (4,7)- --.

Column 28,
Line 7, "5fluoro" should read -- 5-fluoro --.
Line 11, "5propoxy" should read -- 5-propoxy --.
Line 13, "1ylamine" should read -- 1-ylamine --.
Line 14, "5isobutoxy" should read -- 5-isobutoxy --.
Line 17, "3-isoindol" should read -- 3H-isoindol --.
Lines 39, 40 and 51, "1one" should read -- 1-one --.
Line 42, "3amino" should read -- 3-amino --.
Line 44, "3-amino-6-methyl-isoindol-1 1-one" should read -- 3-amino-6-methyl-isoindol-1-one --.
Line 49, "1oxo" should read -- 1-oxo --.
Line 65, "dihydro-[1,4]" should read -- dihydro[1,4] --.

Column 29,
Line 3, "2-1-imino-3-oxo-1,3-" should read -- 2-(1-imino-3-oxo-1,3- --.
Line 21, "hydrochloride" should read -- hydrochlorides --.
Line 30, "of" should read -- for --.
Lines 51 and 63, "groups," should read -- groups; --.
Line 64, "-$OR_1$ groups" should read -- -$OR_i$ groups --.

UNITED STATES PATENT AND TRADEMARK OFFICE
CERTIFICATE OF CORRECTION

PATENT NO. : 6,451,067 B1
DATED : September 17, 2002
INVENTOR(S) : Alain Lagrange et al.

It is certified that error appears in the above-identified patent and that said Letters Patent is hereby corrected as shown below:

Column 30,
Line 6, "diakylamino" should read -- dialkylamino --.
Line 9, after "wherein" insert a colon.
Line 10, "$R_1$" should read -- $R_i$ --.
Line 16, "groups," should read -- groups; --.
Line 18, "N-alkylaminosulphonyalkyl" should read -- N-alkylaminosulphonylalkyl --.
Line 20, "alkylsulphonyl" should read -- alkylsulphonylalkyl --.
Lines 20-21, "alkylcarbonyalkyl" should read -- alkylcarbonylalkyl --.
Line 26, "groups;" should read -- groups, --.
Line 49, after "wherein" insert a colon.
Line 66, "cyano ($C_1$-$C_6$)alkyl" should read -- cyano($C_1$-$C_6$)alkyl --.

Column 31,
Line 8, "R'''" " should read -- R''' --.
Line 11, after "$C_2$-$C_6$" insert a space.
Line 13, "$C_2$-$C_8$" should read -- $C_2$-$C_6$ --.
Line 15, "($C_1$-$C_6$)-alkyl" should read -- ($C_1$-$C_6$)alkyl --.
Line 17, "($C_1$-$C_6$)-alkylcarboxy" should read -- ($C_1$-$C_6$)alkylcarboxy --.
Line 20, "$C_2$ -$C_6$" should read -- $C_2$-$C_6$ --.
Line 32, "($C_1C_6$)" should read -- ($C_1$-$C_6$) --.
Line 58, "$X^8$" should read -- $X^{\ominus}$ --.
Line 64, "diimindoisoindoline" should read -- diiminoisoindoline --.

Column 34,
Line 3, after "attached" insert a comma.
Line 60, "of weight" should read -- by weight --.
Line 66, "glycols ethers;" should read -- glycols; glycol ethers; --.

Column 35,
Line 15, "of weight" should read -- by weight --.

Column 36,
Line 18, before "ethyl" delete the space.
Line 31, "1-bis" should read -- 1,4-bis --.
Line 60, after "3-[3" delete the space.

UNITED STATES PATENT AND TRADEMARK OFFICE
CERTIFICATE OF CORRECTION

PATENT NO. : 6,451,067 B1
DATED : September 17, 2002
INVENTOR(S) : Alain Lagrange et al.

It is certified that error appears in the above-identified patent and that said Letters Patent is hereby corrected as shown below:

Column 37,
Line 42, "{3"-aminoanilino)-N-propyl]}" should read -- {3'-[(4"-aminoanilino)-N-propyl]} --.
Line 45, "(4"amino-2"-methylanilino)" should read -- (4"-amino-2"-methylanilino) --.
Line 52, "1,4-bis-1-(5-amino-2-hydroxybenzyl)" should read -- 1,4-bis-1-[3-(5-amino-2-hydroxybenzyl) --.

Column 38,
Line 18, "(3,5-dimethyl-4-" should read -- (3,5)-dimethyl-4- --.
Lines 29 and 30, "hydroxyethyl" should read -- hydroxyethoxy --.
Line 32, "hydroxyaldehyde" should read -- hydroxybenzaldehyde --.
Line 34, " 3monotrifluorobenzaldehyde" should read -- 3-monotrifluorobenzaldehyde --.
Line 39, "(2,3,4-" should read -- (2,3,4)- --.
Line 41, "(2,4,5-" should read -- (2,4,5)- --.
Line 43, "(2,6)dinitrobenzaldehyde" should read -- (2,6)-dinitrobenzaldehyde --.
Line 53, "1-mono-hydroxy-2-" should read -- 1-monohydroxy-2- --.
Line 57, "carboxyaldehyde" should read -- carboxaldehyde --.
Line 58, "(3,2,1-1J)" should read -- (3,2,1-IJ) --.

Column 39,
Line 32, "isatin-5sulphonic" should read -- isatin-5-sulphonic --.
Line 57, "5hydroxy" should read -- 5-hydroxy --.

Column 40,
Lines 6, 8, 9, 12, 16 and 22, "3imino" should read -- 3-imino --.
Lines 12 and 15, "1ylamine" should read -- 1-ylamine --.
Line 14, "5butoxy" should read -- 5-butoxy --.
Line 16, "5tert" should read -- 5-tert --.
Line 24, "bis(trifluoromethyl)3H" should read -- bis(trifluoromethyl)-3H --.
Line 31, "isoindole" should read -- isoindol --.
Lines 37 and 39, "5ylamine" should read -- 5-ylamine --.
Line 40, "aminosoindol" should read -- aminoisoindol --.
Line 44, "3amino" should read -- 3-amino --.
Line 50, "1oxo" should read -- 1-oxo --.
Line 50, after "carboxylate" insert a semicolon.
Line 54, "7tetrachloroisoindol" should read -- 7-tetrachloroisoindol --.
Line 57, "3-methylamino-isoindol-1-one" should read -- 3-methylaminoisoindol-1-one --.
Line 66, "dihydro-[1,4]" should read -- dihydro[1,4] --.

UNITED STATES PATENT AND TRADEMARK OFFICE
CERTIFICATE OF CORRECTION

PATENT NO. : 6,451,067 B1
DATED : September 17, 2002
INVENTOR(S) : Alain Lagrange et al.

It is certified that error appears in the above-identified patent and that said Letters Patent is hereby corrected as shown below:

Column 41,
Line 7, "(3hydroxypropyl)" should read -- (3-hydroxypropyl) --.
Line 57, "$R_3$and" should read -- $R_3$ and --.

Column 42,
Line 9, "-$OR_1$ groups" should read -- -$OR_i$ groups --.
Line 9, "-$SR_1$ groups" should read -- -$SR_i$ groups --.
Line 9, "-$SR_1Z$ groups" should read -- -$SR_iZ$ groups --.
Line 20, after "wherein" insert a colon.
Line 21, "$R_1$" should read -- $R_i$ --.
Line 22, "groups," should read -- groups; --.
Lines 28-29, "tri-fluoroalkyl fluoroalkyl groups" should read -- trifluoroalkyl groups --.
Line 29, "aminosulphonyalkyl" should read -- aminosulphonylalkyl --.
Lines 33-34, "alkylcarbonyalkyl" should read -- alkylcarbonylalkyl --.
Line 62, after "wherein" insert a colon.

Column 43,
Line 28, "$(C_1-C_6)$-alkyl" should read -- $(C_1-C_6)$alkyl --.
Line 30, "$(C_1-C_6)$-alkylcarboxy" should read -- $(C_1-C_6)$alkylcarboxy --.

Column 44,
Line 4, "$(C_1-C_6$alkyl" should read -- $(C_1-C_6)$alkyl --.
Line 10, after "attached" insert -- to --.
Line 14, "(III)" should read -- (II) --.
Line 26, "$X^8$" should read -- $X^\ominus$ --.

Signed and Sealed this

Twenty-fifth Day of March, 2003

JAMES E. ROGAN
*Director of the United States Patent and Trademark Office*